United States Patent [19]

Cercek et al.

[11] Patent Number: 5,166,052
[45] Date of Patent: Nov. 24, 1992

[54] METHOD FOR MEASURING POLARIZATION OF BATHOCHROMICALLY SHIFTED FLUORESCENCE

[76] Inventors: Boris Cercek; Lea Cercek, both of 4318 Camphor Ave., Yorba Linda, Calif. 92686

[21] Appl. No.: 222,115

[22] Filed: Jul. 20, 1988

Related U.S. Application Data

[63] Continuation-in-part of Ser. No. 867,079, May 27, 1986, abandoned.

[51] Int. Cl.$^5$ .................... G01N 21/76; G01N 33/56; G01N 21/64
[52] U.S. Cl. .................... 435/7.24; 435/172; 356/364; 250/361 L; 250/458.1; 250/461.2
[58] Field of Search .............. 356/318, 319, 322, 323, 356/368, 363, 320, 64; 250/361 C, 363.1, 458.1, 461.1, 461.2, 365, 459.1; 436/546, 808, 800, 172; 435/7, 7.24

[56] References Cited

U.S. PATENT DOCUMENTS

| | | | |
|---|---|---|---|
| 3,897,155 | 7/1975 | Smythe | 356/317 |
| 4,131,800 | 12/1978 | Bruck et al. | 250/461 B |
| 4,284,412 | 8/1981 | Hansen et al. | 436/868 |
| 4,299,486 | 11/1981 | Nogami et al. | 356/318 |
| 4,699,512 | 10/1987 | Koshi | 356/318 |

FOREIGN PATENT DOCUMENTS 0055914 12/1981 European Pat. Off.

OTHER PUBLICATIONS

M. G. Bodea and S. Georghiou; Versatile Nanosecond Fluorometer Employing a Boxcar Averager.

L. Cercek, B. Cercek, and C. I. V. Franklin, "Biophysical Differentiation Between Lymphocytes from Healthy Donors, Patients with Malignant Diseases, and Other Disorders," *Brit. J. Cancer* 29, 345–352 (1974).

L. Cercek & B. Cercek, "Application of the Phenomenon of Changes in the Structuredness of Cytoplasmic Matrix (SCM) in the Diagnosis of Malignant Disorders: a Review," *Europ. J. Cancer* 13, 903–915 (1977).

(List continued on next page.)

Primary Examiner—David L. Lacey
Assistant Examiner—Thomas E. Daley
Attorney, Agent, or Firm—Sheldon & Mak

[57] ABSTRACT

An improved method for measuring polarized fluorescence emissions compensates for background emissions without separating a fluorescing material from background material contributing background fluorescence. The method is particularly useful in measuring fluorescence from a suspension of cells such as stimulated lymphocytes in the SCM assay, where the intracellular fluorescence is due to the penetration of the cells by a fluorogenic agent precursor and its subsequent hydrolysis. The method involves measuring the horizontally and vertically polarized components of the fluorescence emission at a primary wavelength and at least one secondary wavelength. The secondary wavelength is selected based on the bathochromic shift of the spectrum of the fluorescence emissions from the fluorescing material as compared to the fluorescence emissions from the background. From these measurements a factor representing the fraction of the total intensity of fluorescence emission due to background fluorescence at the primary wavelength is determined, from which the intensities of the vertically and horizontally polarized fluorescence emissions due to background fluorescence are derived. These derived background intensities are then subtracted from the vertically and horizontally polarized fluorescence emission intensities measured at the primary wavelength to obtain intensities due solely to the material being analyzed. More than one secondary wavelength can be used to increase the accuracy of the method. Apparatus suitable for practicing this method is described.

54 Claims, 4 Drawing Sheets

OTHER PUBLICATIONS

L. Cercek & B. Cercek, "Studies on the Structuredness of Cytoplasm and Rates of Enzymatic Hydrolysis in Growing Yeast Cells. I. Changes Induced by Ionizing Radiation," *Int. J. Radiat. Biol.* 21, 445–453 (1972).

L. Cercek & B. Cercek, "Studies on the Structuredness of Cytoplasm and Rates of Enzymatic Hydrolysis in Growing Yeast Cells. II. Changes Induced by Ultra Violet Light," *Int. J. Radiat. Biol.* 22, 539–544 (1972).

L. Cercek & B. Cercek, "Relationship Between Changes in the Structuredness of Cytoplasm and Rate Constants for the Hydrolysis of FDA in *Saccharomyces cerevisiae*," *Biophysik* 9, 109–112 (1973).

L. Cercek, B. Cercek, and C. H. Ockey, "Structuredness of the Cytoplasmic Matrix and Michaelis–Menten Constants for the Hydrolysis of FDA During the Cell Cycle in Chinese Hamster Ovary Cells," *Biophysik* 10, 187–194 (1973).

B. I. Lord, L. Cercek, B. Cercek, G. P. Shah, T. M. Dexter, & L. G. Lajtha, "Inhibitors of Haemopoietic Cell Proliferation: Specificity of Action Within the Haemopoietic System," *Brit. J. Cancer* 29, 168–175 (1974).

L. Cercek & B. Cercek, "Involvement of Cyclic–AMP in Changes of the Structuredness of Cytoplasmic Matrix (SCM)," *Radiat. & Environ. Biophys.* 11, 209–212 (1974).

L. Cercek, P. Milenkovic, B. Cercek, & L. G. Lajtha, "Induction of PHA Response In Mouse Bone Marrow Cells by Thymic Extracts as Studied by Changes in the Structuredness of Cytoplasmic Matrix," *Immunology* 29, 885–891 (1975).

L. Cercek & B. Cercek, "Effect of Osmomolarity, Calcium and Magnesium Ions on the Structuredness of Cytoplasmic Matrix (SCM)," *Radiat. & Environ. Biophys.* 13, 9–12 (1976).

L. Cercek & B. Cercek, "Changes in the Structuredness of Cytoplasmic Matrix (SCM) Induced in Mixed Lymphocyte Interactions," *Radiation & Environmental Biophysics* 13, 71–74 (1976).

L. Cercek & B. Cercek, "Involvement of Mitochondria in Changes of Fluorescein Excitation and Emission Polarization Spectra in Living Cells," *Biophys. J.* 28, 403–412 (1979).

L. Cercek, B. Cercek & C. H. Ockey, "Fluorescein Excitation and Emission Polarization in Living Cells: Changes During the Cell Cycle," *Biophys. J.* 23, 395–405 (1978).

L. Cercek, B. Cercek, and B. I. Lord, "Effect of Specific Growth Inhibitors on Fluorescein Fluorescence Polarization Spectra in Haemopoietic Cells," *Brit. J. Cancer* 44, 749–752 (1981).

L. Cercek & B. Cercek, "Effects of Ascorbate Ions on Intracellular Fluorescein Emission Polarization Spectra in Cancer and Normal Proliferating Cells," *Cancer Detection & Prevention* 10, 1–20 (1987).

L. Cercek, B. Cercek, & J. V. Garrett, "Biophysical Differentiation Between Normal Human and Chronic Lymphocytic Leukaemia Lymphocytes," in *Lymphocyte Recognition and Effector Mechanisms* (K. Lindahl-Kiessling and D. Osoba eds., New York, Academic Press, 1974), pp. 553–558.

L. Cercek & B. Cercek, "Changes in the SCM Response Ratio (RRscm) After Surgical Removal of Malignant Tissue," *Brit. J. Cancer* 31, 250–251 (1975).

L. Cercek & B. Cercek, "Apparent Tumour Specificity with the SCM Test," *Brit. J. Cancer* 31, 252–253 (1975).

L. Cercek & B. Cercek, "Changes in the Structuredness of Cytoplasmic Matrix of Lymphocytes as a Diagnostic and Prognostic Test for Cancer," in *Cell Biology and Tumour Immunology, Excerpta Medica International Congress Series No. 349, Proceedings of the XI International Cancer Congress,* Florence, 1974 (Amsterdam, Excerpta Medica, 1974), vol. 1, pp. 318–323).

L. Cercek & B. Cercek, "Detection of Malignant Diseases by Changes in the Structuredness of Cytoplasmic Matrix of Lymphocytes Induced by Phytohaemagglutinin and Cancer Basic Proteins," in *Tumour Markers, Determination and Clinical Role: Proceedings of the Sixth Tenovus Workshop,* Cardiff, Apr., 1977 (K. Griffith, A. M. Neville, and C. G. Pierrepoint, eds., Cardiff, Alpha Omega Publishing Co., 1978), pp. 215–226.

L. Cercek and B. Cercek, "Changes in SCM-Response of Lymphocytes in Mice After Implanation with Ehrlich Ascites Cells," *Europ. J. Cancer* 17, 167–171 (1981).

F. Takaku, T. Yamanaka, and Y. Hashimoto, "Usefulness of the SCM Test in the Diagnosis of Gastric Cancer," *Brit. J. Cancer* 36, 810–813 (1977).

H. Kreutzmann, T. M. Fliedner, H. J. Galla, and E. Sackmann, "Fluorescence-Polarization Changes in Mononuclear Blood Leucocytes After PHA Incubation: Difference in Cells from Patients with and without Neoplasia," *Brit. J. Cancer* 37, 797–805 (1978).

(List continued on next page.)

OTHER PUBLICATIONS

Y. Hashimoto, T. Yamanaka, and F. Takaku, "Differentiation Between Patients with Malignant Disease and Non-Malignant Disease or Healthy Donors by Changes of Fluorescence Polarization in the Cytoplasm of Circulating Lymphocytes," *Gann* 69, 145–149 (1978).

J. A. V. Pritchard and W. H. Sutherland, "Lymphocyte Response to Antigen Stimulation as Measured by Fluorescence Polarization (SCM Test)," *Brit. J. Cancer* 38, 339–343 (1978).

J. A. V. Pritchard, J. E. Seaman, I. H. Evans, K. W. James, W. H. Sutherland, T. J. Deeley, I. J. Kerby, and I. C. M. Patterson, "Cancer-Specified Density Changes in Lymphocytes After Stimulation with Phytohaemagglutinin," *Lancet* 11, 1275–1278 (Dec. 16, 1978).

H. Orjasaeter, G. Jordfald, and I. Svendsen, "Response of T Lymphocytes to Phytohaemagglutinin (PHA) and to Cancer-Tissue-Associated Antigens, Measured by the Intracellular Fluorescence Polarization Technique (SCM Test)," *Brit. J. Cancer* 40, 628–633 (1979).

N. D. Schnuda, "Evaluation of Fluorescence Polarization of Human Blood Lymphocytes (SCM Test) in the Diagnosis of Cancer," *Cancer* 46, 1164–1173 (1980).

J. A. V. Pritchard, W. H. Sutherland, J. G. Siddall, A. J. Bater, I. J. Kerby, T. J. Deeley, G. Griffith, R. Sinclair, B. H. Davies, A. Rimmer, and D. J. T. Webster, "A Clinical Assessment of Fluorescence Polarization Changes in Lymphocytes Stimulated by Phytohaemagglutinin (PHA) in Malignant and Benign Diseases," *Eur. J. Cancer, Clin. Oncol.* 18, 651–659 (1982).

G. R. Hocking, J. M. Rolland, R. C. Nairn, E. Pihl, A. M. Cuthbertson, E. S. R. Hughes, and W. R. Johnson, "Lymphocyte Fluorescence Polarization Changes After Phytohaemagglutinin Stimulation in the Diagnosis of Colorectal Carcinoma," *J. National Cancer Inst.* 68, 579–583 (1982).

M. Deutsch & A. Weinreb, "Validation of the SCM-Test for the Diagnosis of Cancer," *Eur. J. Cancer, Clin. Oncol.* 19, 187–193 (1983).

S. Chaitchik, O. Asher, M. Deutsch, & A. Weinreb, "Tumour Specificity of the SCM Test for Cancer Diagnosis," *Eur. J. Cancer, Clin. Oncol.* 21, 1165–1170 (1985).

J. Matsumoto, T. Tenzaki, and T. Ishiguro, "Clinical Evaluation of Fluorescein Polarization of Peripheral Lymphocytes (SCM Test) in the Diagnosis of Cancer," *J. Japan Soc. Cancer Ther.* 20, 728–734 (1985).

R. D. Spencer and G. Weber, "Influence of Brownian Rotations and Energy Transfer upon the Measurements of Fluorescence Lifetime," *J. Chem. Phys.* 52, 1654–1663.

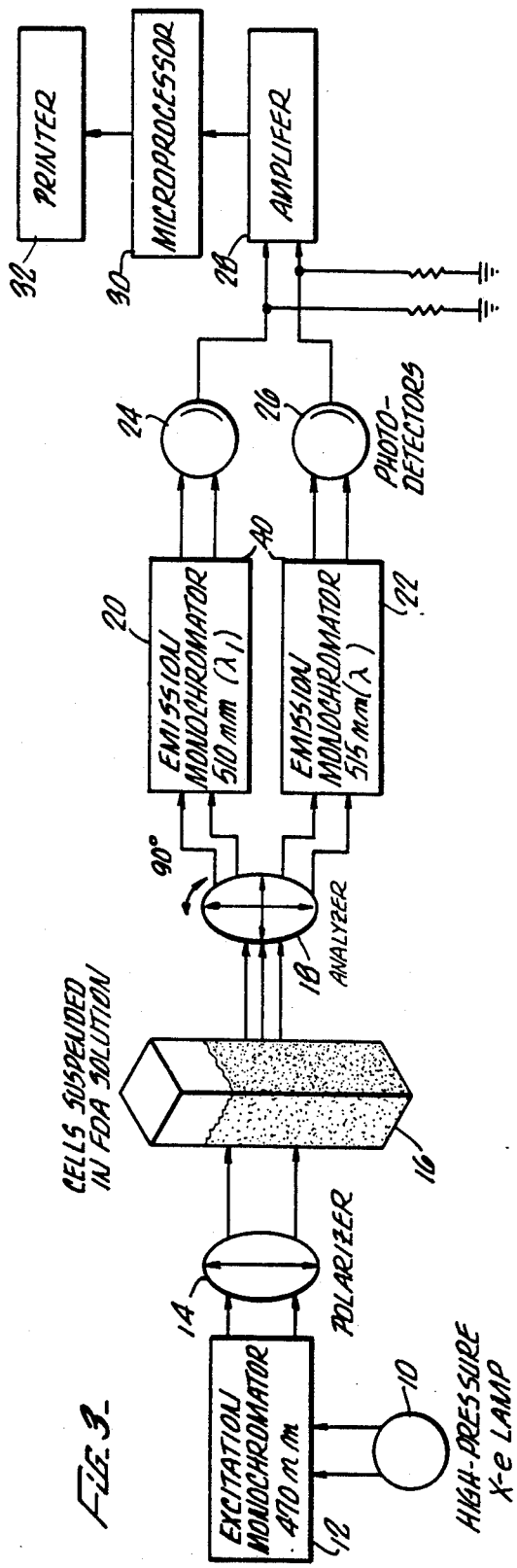
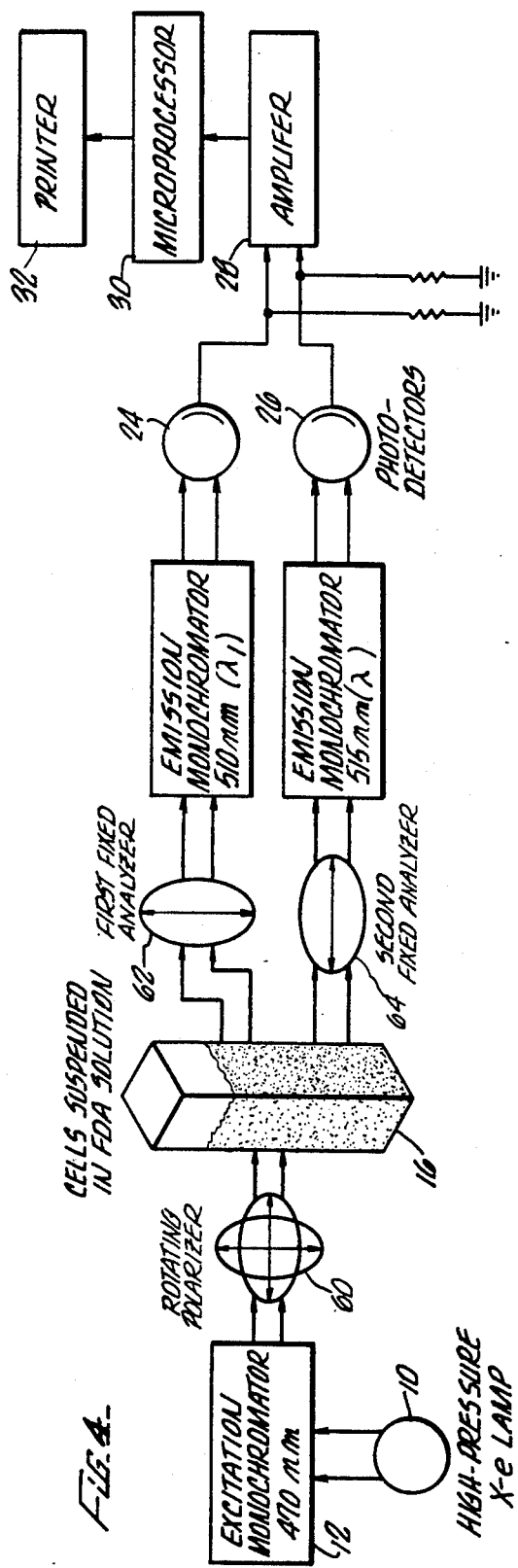

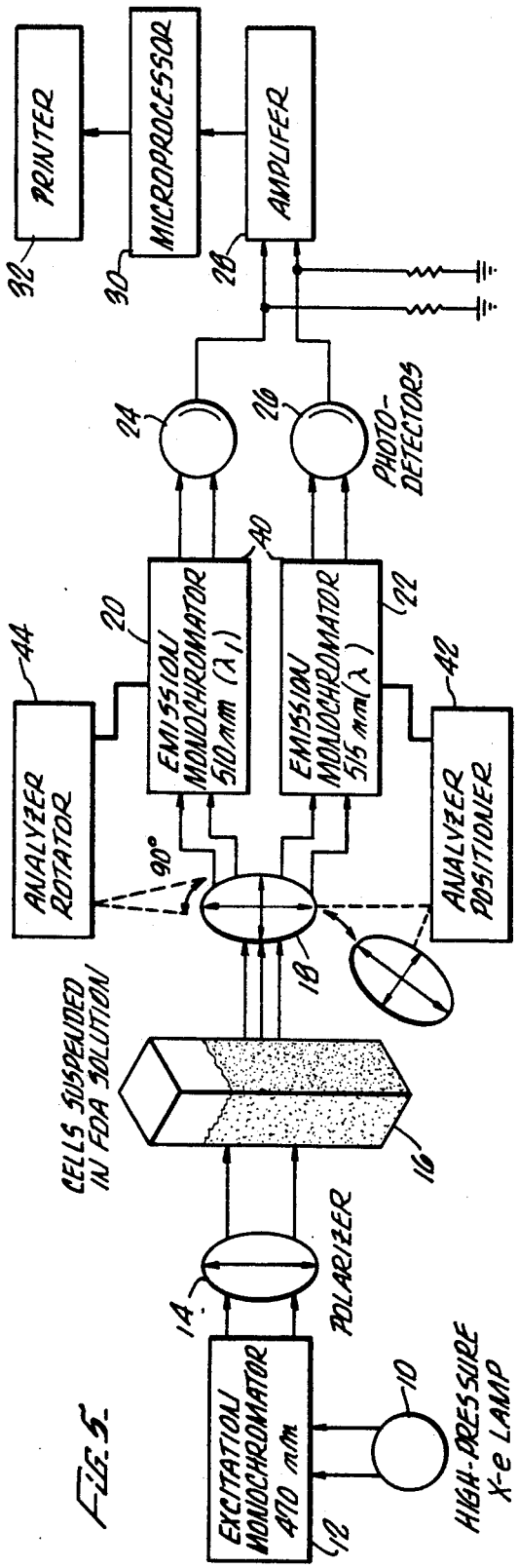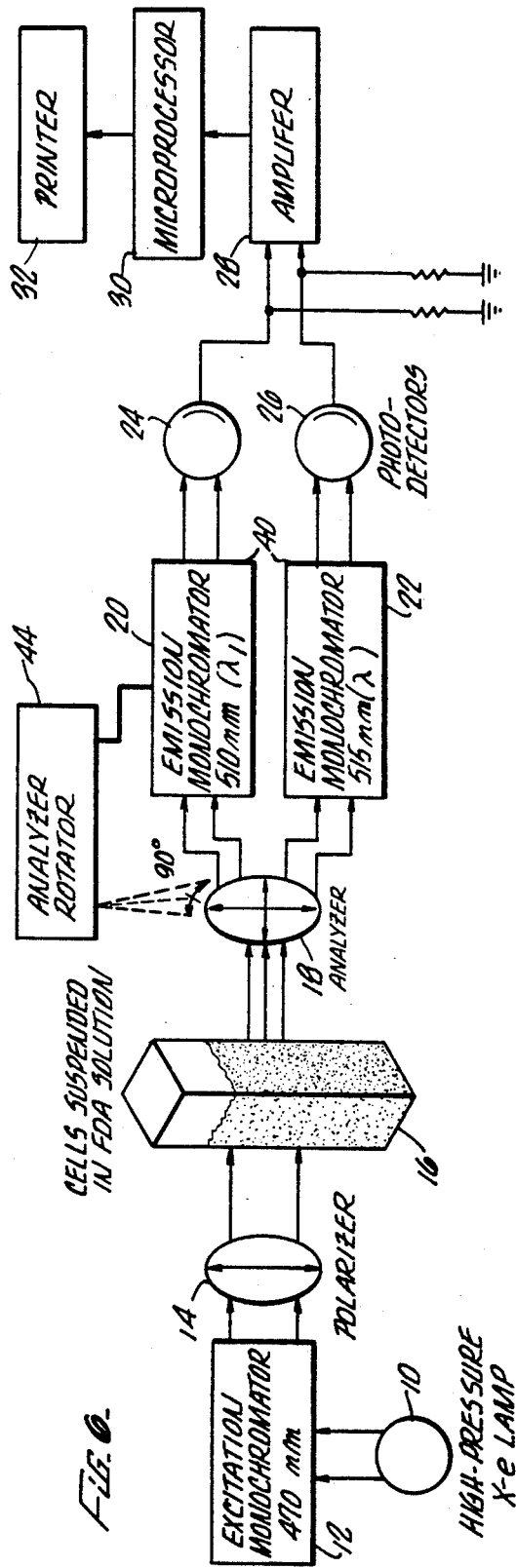

METHOD FOR MEASURING POLARIZATION OF BATHOCHROMICALLY SHIFTED FLUORESCENCE

CROSS-REFERENCE

This application is a continuation-in-part application of U.S. patent application Ser. No. 867,079, entitled "Method for Measuring Polarized Fluorescence Emissions," filed May 27, 1986, now abandoned, and incorporated herein by this reference.

BACKGROUND

Many diseases occurring in humans and animals can be detected by the presence of foreign substances, particularly in the blood, which are specifically associated with the disease or condition. Tests for antigens or other such substances produced as a result of such diseases show great promise as a diagnostic tool for the early detection and treatment of the particular disease that produced the antigen or other substance. Procedures for the detection of such substances must be reliable, reproducible, and sensitive in order to constitute a practical diagnostic procedure for health care providers. In addition, any such procedure should be able to be carried out by persons of ordinary skill and training in laboratory procedure, and should be relatively fast and inexpensive. Preferably, such procedures should be readily adaptable to instrumentation and automation, as required if such procedures are to be carried out on a large scale.

For example, in the treatment of the various malignancies that afflict humans and animals, referred to generally as cancer, it is recognized that early detection is a key to effective treatment, especially as many therapeutic procedures are effective only in relatively early stages of the disease. In fact, virtually all known cancer treatments are not only more effective, but safer, when administered in early stages of cancer. Far too many cases of cancer are only discovered too late for effective treatment.

Accordingly, there is a great need for rapid, easy-to-perform, and reliable tests which can diagnose cancer at early stages. In this connection new tests and procedures are being developed to effect early diagnosis of the cancer.

We have developed and reported one such test for the early detection of cancer in L. Cercek, B. Cercek, and C.I.V. Franklin, "Biophysical Differentiation Between Lymphocytes from Healthy Donors, Patients with Malignant Diseases and Other Disorders," *Brit. J. Cancer* 29, 245-352 1974) and L. Cercek and B. Cercek, "Application of the Phenomenon of Changes in the Structuredness of Cytoplasmic Matrix (SCM) in the Diagnosis of Malignant Disorder: a Review," *Europ. J. Cancer* 13, 903-915 (1977), which are incorporated herein by this reference.

Our basic SCM test includes the steps of:
(1) challenging a selected subpopulation of lymphocytes from a donor with a challenging agent such as a mitogen or an antigen associated with a condition or disease, such as cancer; and
(2) determining the change in structuredness of the cytoplasmic matrix (SCM) of the challenged lymphocytes, typically using fluorescence polarization.

When applied to cancer, our SCM (structuredness of cytoplasmic matrix) test is based on the phenomenon that the internal structure of a selected subpopulation of the lymphocytes from a healthy individual is altered when challenged by a mitogen such as phytohaemagglutinin (PHA) but is not altered by other selected challenging agents, such as certain cancerassociated antigens. Contrarily, the equivalent subpopulation of lymphocytes from an individual with cancer responds oppositely. In other words the same subpopulation of lymphocytes from cancer patients does not respond in the SCM test when challenged by a mitogen, but does respond strongly to challenge by a number of cancer-associated antigens.

The change seen in SCM are believed to reflect changes in the internal structure of the lymphocyte as the lymphocyte is activated for synthesis. Similar changes can occur in living cells other than lymphocytes during the cell cycle and growth of the cells. Such changes can also be evoked by various external agents, such as ionizing radiation, mechanical forces, chemicals, growth inhibiting and stimulating agents, etc. These changes can be conveniently monitored with a specially adapted technique of fluorescein fluorescence polarization, as we have published in numerous articles, including L. Cercek and B. Cercek, "Studies on the Structuredness of Cytoplasm and Rates of Enzymatic Hydrolysis in Growing Yeast Cells. I. Changes Induced by Ionizing Radiation," *Int. J. Radiat. Biol.* 21, 445-453 (1972); L. Cercek and B Cercek, "Studies on the Structuredness of Cytoplasm and Rates of Enzymatic Hydrolysis in Growing Yeast Cells. II. Changes Induced by Ultra-Violet Light," *Int. J. Radiat. Biol* 22. 539-544 (1972); L. Cercek and B. Cercek, "Relationship Between Changes in the Structuredness of Cytoplasm and Rate Constants for the Hydrolysis of FDA in *Saccharomyces cerevisiae*," *Biophysik* 9, 109-112 (1973); L. Cercek, B. Cercek, and C. H. Ockey, "Structuredness of the Cytoplasmic Matrix and Michaelis-Menten Constants for the Hydrolysis of FDA During the Cell Cycle in Chinese Hamster Ovary Cells," *Biophysik* 10 187-194 (1973) B. I. Lord, L. Cercek, B. Cercek, G. P. Shah, T. M. Dexter and L. G. Lajtha, "Inhibitors of Haemopoietic Cell Proliferation: Specificity of Action Within the Haemopoietic System," *Brit. J. Cancer* 29 168-175 (1974); L. Cercek and B. Cercek, "Involvement of Cyclic-AMP in Changes of the Structuredness of Cytoplasmic Matrix," *Radiat. & Environ. Biophys.* 11, 209-212 (1974); L. Cercek, P. Milenkovic, B. Cercek, & L. G. Lajtha, "Induction of PHA Response in Mouse Bone Marrow Cells by Thymic Extracts as Studied by Changes in the Structuredness of Cytoplasmic Matrix," *Immunology* 29, 885-891 (1975); L. Cercek and B. Cercek, "Effects of Osmomolarity, Calcium and Magnesium Ions on the Structuredness of Cytoplasmic Matrix (SCM)," *Radiat. & Environ. Biophys.* 13, 9-12 (1976); L. Cercek & B. Cercek, "Changes in the Structuredness of Cytoplasmic Matrix (SCM) Induced in Mixed Lymphocyte Reactions," *Radiat. & Environ. Biophys.* 13, 71-74 (1976); L. Cercek, B. Cercek, & C. H. Ockey, "Fluorescein Excitation and Emission Polarization Spectra in Living Cells: Changes During the Cell Cycle," *Biophys. J.* 23, 395-405 (1978) L. Cercek and B. Cercek, "Involvement of Mitochondria in Changes of Fluorescence Excitation and Emission Polarization Spectra in Living Cells," *Biophys. J.* 28, 403-412 (1979); L. Cercek, B. Cercek, and B. I. Lord, "The Effect of Specific Growth Inhibitors on Fluorescein Fluorescence Polarization Spectra in Haemopoietic Cells," *Brit. J. Cancer,* 44 749-752 (1981); and L. Cercek and B. Cercek, "Effects of Ascorbate Ions on Intracellular Fluorescein Emission Polarization Spectra in Cancer and Normal Proliferating Cells," *Cancer Detection and Prevention* 10, 1–20 (1987), all of which are incorporated herein by this reference.

The usefulness of this SCM test for the detection of cancer has been documented in numerous articles. Articles from our laboratory include: L. Cercek, B. Cercek, and J. V. Garrett, "Biophysical Differentiation Between Normal Human and Chronic Lymphocytic Leukaemia Lymphocytes," in *Lymphocyte Recognition and Effector Mechanisms* (K. Lindahl-Kiessling and D. Osoba eds., New York, Academic Press, 1974), pp. 553–558; L. Cercek, B. Cercek and C. I. V. Franklin, "Biophysical Differentiation between Lymphocytes from Healthy Donors, Patients with Malignant Disease and Other Disorders," *Brit. J. Cancer* 29 345–352 (1974); L. Cercek and B. Cercek, "Changes in the SCM Response Ratio ($RR_{SCM}$) After Surgical Removal of Malignant Tissue," *Brit. J. Cancer* 31, 250–251 (1975); L. Cercek and B. Cercek, "Apparent Tumour Specificity with the SCM Test," Brit. J. Cancer 31, 252–253 (1975); L. Cercek and B. Cercek, "Changes in the Structuredness of Cytoplasmic Matrix of Lymphocytes as a Diagnostic and Prognostic Test for Cancer," in *Cell Biology and Tumour Immunology, Excerpta Medica International Congress Series No. 349, Proceedings of the XI International Cancer Congress, Florence,* 1974 (Amsterdam, Excerpta Medica, 1974), vol. 1, pp. 318–323) L. Cercek and B. Cercek, "Application of the Phenomenon of Changes in the Structuredness of Cytoplasmic Matrix (SCM) in the Diagnosis of Malignant Disorders: a Review," *Europ. J. Cancer* 13, 903–915 (1977); L. Cercek and B. Cercek, "Detection of Malignant Diseases by Changes in the Structuredness of Cytoplasmic Matrix of Lymphocytes Induced by Phytohaemagglutinin and Cancer Basic Proteins," in *Tumour Markers, Determination and Clinical Role: Proceedings of the Sixth Tenovus Workshop, Cardiff, April* 1977 (K., Griffith, A. M. Neville, and C. G. Pierrepoint, eds., Cardiff, Alpha Omega Publishing Co., 1978), pp. 215–226; and L. Cercek and B. Cercek, "Changes in SCM-Responses of Lymphocytes in Mice After Implantation with Ehrlich Ascites Cells," *Europ. J. Cancer* 17, 167–171 (1981), all of which are incorporated herein by this reference.

The usefulness of the SCM test has been confirmed in articles from other laboratories, including F. Takaku, K. Yamanaka, and Y. Hashimoto, "Usefulness of the SCM Test in the Diagnosis of Gastric Cancer," *Brit. J. Cancer* 36, 810–813 (1977); H. Kreutzmann, T. M. Fliedner, H. J. Galla, and E. Sackmann, "FluorescencePolarization Changes in Mononuclear Blood Leucocytes After PHA Incubation: Differences in Cells from Patients with and Without Neoplasia," *Brit. J. Cancer* 37, 797–805 (1978); Y. Hashimoto, T. Yamanaka, and F. Takaku, "Differentiation Between Patients with Malignant Diseases and Non-Malignant Diseases or Healthy Donors by Changes of Fluorescence Polarization in the Cytoplasm of Circulating Lymphocytes," *Gann* 69, 145–149 (1978); J. A. V. Pritchard and W. H. Sutherland, "Lymphocyte Response to Antigen Stimulation as Measured by Fluorescence Polarization (SCM-Test)," *Brit. J. Cancer* 38, 339–343 (1978); J. A. V. Pritchard, J. E. Seaman, I. H. Evans, K. W. James, W. H. Sutherland, T. J. Deeley, I. J. Kerby, I. C. M. Patterson, and B. H. Davies, "Cancer-Specific Density Changes in Lymphocytes Following Stimulation with Phytohaemagglutinin," *Lancet* 11, 1275–1277 (Dec. 16. 1978); H. Orjasaeter, G. Jordfald, and I. Svendsen, "Response of T-Lymphocytes to Phytohaemagglutinin (PHA) and to Cancer-Tissue-Associated Antigens, Measured by the Intracellular Fluorescence Polarization Technique (SCM Test)," *Brit. J. Cancer* 40, 628–633 (1979); N. D. Schnuda, "Evaluation of Fluorescence Polarization of Human Blood Lymphocytes (SCM Test) in the Diagnosis of Cancer," Cancer 46, 1164–1173 (1980); J. A. V. Pritchard, W. H. Sutherland, J. E. Siddall, A. J. Bater, I. J. Kerby, T. J. Deeley, G. Griffith, R. Sinclair, B. H. Davies, A. Rimmer, & D. J. T. Webster, "A Clinical Assessment of Fluorescence Polarisation Changes in Lymphocytes Stimulated by Phytohaemagglutinin (PHA) in Malignant and Benign Disease," *Europ. J. Cancer, Clin. Oncol.* 18, 651–659 (1982); G. R. Hocking, J. M. Rolland, R. C. Nairn, E. Pihl, A. M. Cuthbertson, E. S. R. Hughes, and W. R. Johnson, "Lymphocyte Fluorescence Polarization Changes After Phytohaemagglutinin Stimulation in the Diagnosis of Colorectal Carcinoma," *J. National Cancer Inst.* 68 579–583 (1982); M. Deutsch and A. Weinreb, "Validation of the SCM-Test for the Diagnosis of Cancer," *Eur. J. Cancer, Clin. Oncol.* 19, 187–193 (1983); S. Chaitchik, O. Asher, M. Deutsch. and A. Weinreb, "Tumour Specificity of the SCM Test for Cancer Diagnosis," *Europ. J. Cancer, Clin. Oncol.* 21 1165–1170 (1985); and J. Matsumoto, T. Tenzaki and T. Ishiguro, "Clinical Evaluation of Fluorescein Polarization of Peripheral Lymphocytes (SCM Test) in the Diagnosis of Cancer," *J. Japan Soc. Cancer Ther.* 20, 728–734 (1985), all of which are incorporated herein by this reference.

The SCM test can be applied to detection of diseases and conditions other than cancer, such as viral and bacterial infections, determination of allergic reactions, tissue typing, and monitoring of allograft rejections based on the SCM responses in mixed lymphocyte reactions, as disclosed in the 1976 *Radiation and Environmental Biophysics* article by L. Cercek and B. Cercek. This extension of the SCM test is disclosed and claimed in our co-pending U.S. patent application, Ser. No. 838,264, filed Mar. 10, 1986, now abandoned, and entitled "Separation and Use of Density Specific Blood Cells," which is incorporated herein by this reference. The presence of other antigen-producing diseases and bodily conditions does not interfere with the SCM test; a patient afflicted with more than one type of antigen-producing disease can be tested for a multiplicity of such diseases simply by running separate tests using for each test an antigen derived from each separate disease or condition being tested for.

When fluorescence polarization is used to determine changes of SCM, such changes are seen as a decrease in the fluorescence polarization of the cells when polarized light is used to excite an extrinsic fluor generated intracellularly by the hydrolysis of a nonfluorescent compound which has been absorbed by the lymphocytes. The fluor typically is fluorescein and the nonfluorescent compound is typically fluorescein diacetate (FDA). The FDA serves as a fluorogenic agent precursor. An extrinsic fluor is used because the intrinsic fluorescence of cellular components is too small to give meaningful results in this test. Therefore, all references to fluorescence polarization values herein are references to fluorescence polarization values obtained with an extrinsic fluor, preferably one generated by enzymatic hydrolysis from a nonfluorogenic compound added to and absorbed by the cells.

Fluorescence polarization is a measure of intracellular rigidity; the greater the intracellular mobility, the less the measured fluorescence polarization. As seen in the SCM test, the observed decrease in fluorescence polarization is believed to result mainly from changes in the conformation of the mitochondria, the energy-producing organelles of the cell. The changes in the mitochondria are believed to result from the contractions of the cristae or inner folds of the mitochondrial membrane. The SCM reflects the forces of interaction between macromolecules and small molecules such as water molecules, ions, adenosine triphosphate, and cyclic adenosine monophosphate. Perturbations of these interactions result in changes in the SCM.

In our SCM test, the best indication of structuredness is not the absolute fluorescence polarization measured, but rather the net fluorescence polarization (P). P is determined after correction is made for: (i) intrinsic fluorescence of the medium in which the cells are suspended; (ii) extracellular fluor present whether generated by leakage of fluor from cells or non-enzymatic hydrolysis of fluorescein diacetate in the medium; and (iii) unequal transmission of the two components of polarized light in the fluorescence polarization measurement apparatus. Thus all references to fluorescence polarization below are to net fluorescence polarization, P, unless indicated otherwise. When the fluorescence polarization measurements are performed on living cells, P is the net intracellular polarization.

In our test, fluorescein is introduced into the cells by intracellular hydrolysis of the non-fluorogenic compound fluorescein diacetate which has been taken up by the lymphocytes. Then are measured the horizontally and vertically polarized components of emitted fluorescence due to excitation of the cell suspension by light from a suitable source, such as vertically polarized blue light from a xenon lamp. The intensities of the vertically and horizontally polarized fluorescence components are used to calculate P. Challenged lymphocytes from a donor afflicted with a disease or condition associated with the challenging antigen exhibit a substantial decrease of at least 10 percent in the fluorescence polarization value, P, compared to non-challenged lymphocytes from the same donor. On the other hand, challenged lymphocytes from donors not afflicted with the antigen-producing disease or condition do not exhibit a significant decrease in P after contact with the challenging antigen.

As previously stated, the calculation of P includes corrections for several factors, including background fluorescence, in order to yield meaningful fluorescence polarization values. Ideally, since the FDA or other fluorogenic agent precursor itself does not fluoresce and is only converted into a fluorescent compound such as fluorescein on intracellular hydrolysis by the lymphocytes, the background is relatively small and consists of only the fluorescence resulting from the background material.

In practice, however, compensating for background fluorescence creates serious problems with the SCM measurements. As soon as the intracellular hydrolysis of FDA to fluorescein begins, some of the fluorescein molecules produced by the hydrolysis leak out of the cell and add to background fluorescence. Additionally, FDA is susceptible to nonenzymatic or thermal hydrolysis resulting in still more fluorescein present outside of the cell and a higher background. This background steadily increases as the fluorescence polarization is measured.

In our prior work, we compensated for this extracellular fluorescence background by filtering the lymphocyte suspension. Filtration was begun about four to seven minutes after the recording of polarized fluorescence intensities had begun. The vertically and horizontally polarized components of the fluorescence emissions from the cell-free filtrate as well as the length of time of the filtration step had to be recorded. The fluorescence polarization intensity measurements performed on the lymphocyte suspension before filtering then had to be extrapolated to the time point at which the filtration step was one-half completed, and the fluorescence polarization measurements on the filtrate then subtracted from the extrapolated measurements to obtain the net intracellular vertically and horizontally polarized fluorescence intensities due to the lymphocytes themselves. This measurement process is described in our 1977 *European Journal of Cancer* article.

In unskilled hands, the filtration step can introduce errors and uncertainties into the SCM results. For example, delay in filtration can introduce uncertainties in the values of the extrapolated fluorescence polarization measurements, since the intensity increases with time. In addition, if excess pressure is applied to the cells during filtration, the filtration step itself can damage cell membranes, resulting in leakage of intracellular fluorescein and fluorescein diacetate-hydrolyzing enzyme into the filtrate. This leakage can cause an artificially high background measurement. Not only can the fluorescein leaked into the filtrate directly increase the background fluorescence, but the presence of fluorescein diacetate-hydrolyzing enzyme in the filtrate can convert some of the nonfluorescing fluorescein diacetate into fluorescein, further adding to the background.

Clinical consequences of an erroneously high background measurement can be serious. Because fluorescence polarization is a measure of mobility, the emissions from the free fluorescein released by rupture of the cells or created by hydrolysis in the filtrate are less polarized than that of bound fluorescein within the lymphocytes. The subtraction of this artificially high background from the vertically and horizontally polarized fluorescence intensity measurements on the suspension can lead to the erroneous conclusion that the emissions from the lymphocyte-containing suspension are more polarized than they actually are. If the filtration error occurs on a lymphocyte sample that has been stimulated with a cancer-associated antigen, the result can be a false negative test. This occurs because the apparent polarization actually measured is greater than it should be and the decrease in fluorescence polarization caused by a positive SCM response and indicative of cancer will be masked. Conversely, if the filtration error occurs on a sample of unstimulated control lymphocytes, the result can be a false positive. The apparent polarization value of the control is higher than it should be In this case, another sample of lymphocytes from a normal donor exposed to a cancer-associated antigen but not responding to that antigen gives a lower apparent polarization value if the artificially high background measurement does not occur on that sample. This lower apparent polarization value can be interpreted as indicating the presence of cancer.

There are additional disadvantages associated with the use of the filtration technique to determine the background for fluorescence polarization measurements, especially if large-scale clinical testing is intended. Considerable experience and skill are required to extrapolate the fluorescence measurements accurately and repeatedly over the time period required for filtration. The filtration process is slow, particularly if the pressures used are limited; it requires additional equipment, and is difficult to carry out reproducibly on more than a few samples at a time. Also, the filtration procedure requires rather large volumes of sample, about 3 ml. Although all of these disadvantages can be overcome when the SCM test is used for relatively small-scale laboratory studies, they present serious obstacles to large-scale clinical use of the SCM test.

Accordingly, there is a need for a fluorescence polarization measurement technique capable of compensating for background extracellular fluorescence without using the filtration step. This technique should be rapid, suitable for automation, require a small sample, and be capable of being carried out with a minimum of equipment by workers with a minimum of specialized training. Preferably a large number of samples should be able to be processed with the technique.

SUMMARY

This invention is directed to methods and apparatus for measuring fluorescence polarization that meet the above needs. The measurements are conducted on biological structures such as whole cells, particularly lymphocytes, portions of cells such as mitochondria, viruses, or liposomes. The invention is useful whenever the background in which the fluorescing material is dissolved or suspended contributes fluorescence due to the presence of the same fluor found in the fluorescing material. The invention is particularly useful for measuring fluorescence polarization on lymphocytes in the SCM test.

The invention is based on the discovery that fluorescence from intracellular fluorescein in fluorescence-containing lymphocytes is bathochromically shifted (shifted to longer wavelengths) relative to the background fluorescence due to extracellular fluorescein. The effect of the shift is that the extracellular and intracellular fluorescence can be regarded as originating from two different fluorophores, with two different fluorescence emission spectra and two different fluorescence emission maxima. This allows determination of the proportion of the total fluorescence intensity at any wavelength attributable to either intracellular or extracellular fluorescence.

Most broadly, this invention provides a method for compensating for background fluorescence in the measurement of polarized fluorescence emissions from a fluorescing material in a sample comprising the fluorescing material and background material, the background material contributing background fluorescence. The method yields measurements reflecting the contributions to fluorescence emissions of only the fluorescing material. In the method, there is no need to separate physically the fluorescing material from the background material.

The fluorescing material is generally isotropic in its response to polarized light since the degree of polarization of the emitted fluorescence relative to that of the exciting light does not depend on the orientation of the plane-polarized light used to excite the fluorescing material. Our method is therefore applicable whenever the emitted polarized fluorescence is measured in two planes, with the second plane being transverse to the first plane. Preferably the first plane is parallel to the plane of the exciting plane-polarized light. More preferably the two planes are orthogonal. However, because the conventional fluorescence polarization measuring apparatus excites the fluorescing material with vertically polarized light and measures the emitted polarized light in the vertical and horizontal planes, the equations herein describe that orientation of the exciting light and the two planes of measurement.

Most generally, the method comprises five basic steps. Step (1) comprises exciting the sample with plane-polarized light. Step (2) comprises measuring the polarized emissions from the sample at a first or primary wavelength ($\lambda_1$). The measurements at $\lambda_1$ are made in two planes, a first plane parallel to the plane of polarization of the exciting light and a second plane transverse to the first plane. These measurements yield:

(a) $I_{P1}$, which is the measured fluorescence intensity in the first plane at $\lambda_1$; and (b) $I_{T1}$, which is the measured fluorescence intensity in the second plane at $\lambda_1$.

Step (3) of the method comprises determining at a secondary wavelength ($\lambda_2$) different from $\lambda_1$ and within the range of wavelengths determined by the shift of the fluorescence emission spectrum due to background fluorescence, the total intensity of the fluorescence emissions ($I_{tot2}$).

Step (4) comprises determining from $I_{P1}$, $I_{T1}$, and $I_{tot2}$ the polarized fluorescence emission intensities in the first plane ($I_{P1B}$) and in the second plane ($I_{T1B}$) emitted by the background material at $\lambda_1$.

Step (5) comprises subtracting $I_{P1B}$ from $I_{P1}$ to obtain $I_{P1F}$ and subtracting $I_{T1B}$ from $I_{T1}$ to obtain $I_{T1F}$. $I_{P1F}$ and $I_{T1F}$ are the emission intensities in the two planes due solely to the fluorescing material.

Three alternatives exist for the determination of $I_{tot2}$ in this general method. In the first alternative, measurements of polarized fluorescence emission intensity are made at $\lambda_2$ in the two planes, yielding:

(i) $I_{P2}$, which is the measured fluorescence intensity in the first plane at $\lambda_2$; and 1 (i) $I_{T2}$, which is the measured fluorescence intensity in the second plane at $\lambda_2$. In this alternative, $I_{P1B}$ and $I_{T1B}$ are determined from $I_{P1}$, $I_{P2}$, $I_{T1}$, and $I_{T2}$, and $I_{tot2}$ is obtained as part of the determination of $I_{P1B}$ and $I_{T1B}$.

In the second alternative, $I_{tot2}$, the total intensity of the fluorescence emissions at $\lambda_2$, can be measured directly and used to determine the polarized fluorescence intensities in the first and second planes emitted by the background material.

In either the first or second alternatives, the first and second planes can be orthogonal. If so, typically the exciting plane-polarized light is vertically polarized and the horizontally and vertically polarized emissions from the sample are measured.

In the third alternative, when vertically polarized light is used to excite the sample and measurements of the polarized fluorescence emissions are measured at $\lambda_1$ in the vertical and horizontal planes, $I_{M2}$, the polarized fluorescence emissions at $\lambda_2$ in a plane oriented 54.7° from the vertical, can be measured, whereby the value of $I_{M2}$ is proportional to $I_{tot2}$ regardless of the degree of polarization of the fluorescence emitted by the sample.

Preferably $\lambda_1$ is chosen to be at the maximum of the fluorescence emission spectrum of the fluorescing material. $\lambda_2$ is then preferably selected such that the absolute value of $((I_{tot1F}/I_{tot1B}) - (I_{tot2F}/I_{tot2B}))$ is maximized, where:

(a) $I_{tot1F}$ is the total fluorescence emission intensity from the fluorescing material at $\lambda_1$;

(b) $I_{tot2F}$ is the total fluorescence emission intensity from the fluorescing material at $\lambda_2$;

(c) $I_{tot1B}$ is the total fluorescence emission intensity from the background material at $\lambda_1$; and (d) $I_{tot2B}$ is the total fluorescence emission intensity from the background material at $\lambda_2$. This is equivalent to selecting $\lambda_2$ such that the difference between $K_a$ and $K_b$ is maximized, where:

(1) $K_a$ is a ratio obtained by dividing $I_{tot2B}$ by $I_{tot1B}$, where:

(a) $I_{tot2B}$ is the total fluorescence emission intensity for the background material at $\lambda_2$; and (b) $I_{tot1B}$ is the total fluorescence emission intensity for the background material at $\lambda_1$;

(2) $K_b$ is a similar ratio obtained by dividing $I_{tot2F}$ by $I_{tot1F}$, where:

(a) $I_{tot2F}$ is the total fluorescence emission intensity for the fluorescing material at $\lambda_2$; and (b) $I_{tot1F}$ is the total fluorescence emission intensity for the fluorescing material at $\lambda_1$. Determination of $K_a$ and $K_b$ requires physical separation of the fluorescing material from the background material. $K_a$ and $K_b$ are constants for the particular instrumentation used, but vary with $\lambda_1$ and $\lambda_2$.

Preferably, the difference between $\lambda_1$ and $\lambda_2$ is at least about 5 nm and is no greater than about 10 nm and more preferably, about 15 nm. Only one secondary wavelength, $\lambda_2$, need be used, although more can be used.

When the sample is excited with vertically polarized light and the vertically and horizontally polarized fluorescence emissions therefrom are measured, the method can further comprise the step (5) of determining the net polarization value, P, of the fluorescing material from $I_{P1F}$ and $I_{T1F}$ according to the equation:

$$P = (I_{P1F} - G \times I_{T1F})/(I_{P1F} + G \times I_{T1F}).$$

In this equation, G is a correction factor for the unequal transmission of the vertically and the horizontally polarized fluorescence emissions through the optical system of a fluorescence measuring instrument.

When the exciting light is vertically polarized and the vertically and horizontally polarized fluorescence emissions are measured, the relationships among the intensities can be described by several equations. Step (3) can comprise a series of substeps, namely;

(3a): Obtaining the total fluorescence emissions of the sample at $\lambda_1$ and $\lambda_2$, $I_{tot1}$ and $I_{tot2}$, from $I_{P1}$, $I_{T1}$, $I_{P2}$, and $I_{T2}$ in accordance with the following relationship:

$$I_{tot\lambda} = I_{P\lambda} + 2(I_{T\lambda} \times G).$$

In this equation:

(i) $I_{tot\lambda}$ is the total intensity of the fluorescence emissions from the sample at the wavelength $\lambda$, with $\lambda$ being equal to either $\lambda_1$ or $\lambda_2$;

(ii) $I_{P\lambda}$ and $I_{T\lambda}$ are either $I_{P1}$ and $I_{T1}$ or $I_{P2}$ and $I_{T2}$, depending upon the value of $\lambda$; and (iii) G is a correction factor for the unequal transmission of the vertically and horizontally polarized fluorescence emissions through the optical system of a fluorescence measuring instrument, and is constant for any particular fluorescence measuring instrument. As measured, both $I_{P1}$ and $I_{T1}$ include contributions of fluorescence from both the fluorescing material and the background material.

(3b): Determining a factor F representing the fraction of the total intensity of the fluorescence emissions at $\lambda_1$ due to background fluorescence by the relationship;

$$F = \frac{K_b - Q}{K_b - K_a}.$$

In this equation, $K_a$ and $K_b$ are constants for the instrumentation used and are determined as stated above, and Q is the ratio of $I_{tot2}$ divided by $I_{tot1}$. Q varies from sample to sample with the relative contributions to fluorescence of the fluorescing material and the background material.

(3c) Determining from the factor F the values of $I_{P1B}$ and $I_{T1B}$ according to the relationships:

$$I_{P1B} = \frac{I_{tot1} \times F}{1 + 2(1 - P_k/1 + P_k)},$$

and $$I_{T1B} = \frac{I_{tot1} \times F}{(2 + (1 + P_k/1 - P_k)) \times G},$$

wherein $P_k$ is a constant defined by the relationship:

$$P_k = \frac{I_{P1BS} - G \times I_{T1BS}}{I_{P1BS} + G \times I_{T1BS}},$$

In the equation defining $P_k$, $I_{P1BS}$ and $P_{T1BS}$ are the vertically and horizontally polarized fluorescence emission intensities, respectively, at $\lambda_1$ of the background material in a separate sample from which the fluorescing material has been removed G is the correction factor introduced hereinabove in substep (3a).

Additionally and for greater accuracy, this method can make use of at least one additional secondary wavelength, $\lambda_3$, within the range of wavelengths determined by the shift of the fluorescence emission spectrum due to background fluorescence emissions. When an additional secondary wavelength, $\lambda_3$, is used, the method comprises an additional four steps.

Of these additional four steps, step (a) is the determination of a number of quantities at $\lambda_3$. These quantities are:

(i) the vertically and horizontally polarized fluorescence emissions from the sample, $I_{P3}$ and $I_{T3}$;

(ii) the total fluorescence emission intensity from the background material, $I_{tot3B}$, the fluorescing material having been removed from the sample; and (iii) the total fluorescence emission intensity from the fluorescing material, $I_{tot3F}$.

Step (b) is the determination from $I_{P3}$, $I_{T3}$, $I_{tot3B}$, $I_{tot3F}$, and from the previously determined quantities $I_{P1}$, $I_{T1}$, $I_{tot1B}$, and $I_{tot1F}$, a second value of the factor F, $F_2$. Step (c) is the determination of the average value, $F_{av}$, of the factor F, from the first value of F, $F_1$, which had been previously determined at $\lambda_1$ and $\lambda_2$, and from $F_2$. Step (d) is the use of $F_{av}$ in determining $I_{P1B}$ and $I_{T1B}$.

The bathochromic shift method of the present invention can be applied to fluor-containing lymphocytes and incorporated directly into the SCM test for diagnosing the presence of a condition or disease in a body.

The following preparatory steps are needed to incorporate the general bathochromic shift method into the SCM test:

(1) drawing a sample of lymphocyte-containing body fluid from the body to be tested;

(2) separating SCM-responding lymphocytes from the body fluid;

(3) contacting the SCM-responding lymphocytes with an antigen derived from or associated with the disease or condition being tested for to stimulate the lymphocytes;

(4) forming a suspension of the stimulated lymphocytes and a fluorogenic agent precursor; and (5) maintaining the stimulated lymphocytes in the suspension for sufficient time to allow penetration or the lymphocytes by the fluorogenic agent precursor and the precursor's intracellular hydrolysis to a fluorogenic compound for generating stimulated fluor-containing lymphocytes.

The suspension of the stimulated fluor-containing lymphocytes is then used as the sample in the general bathochromic shift method, or in the modifications previously described in which $I_{tot2}$ or $I_{M2}$ are measured, to obtain $I_{P1F}$ and $I_{T1F}$. These quantities, $I_{P1F}$ and $I_{T1F}$, are then used to determine the SCM response of the fluor-containing lymphocytes to the antigen used to stimulate the lymphocytes. The SCM response of the lymphocytes is an indication of the presence or absence of the tested for disease or bodily condition in the body of the donor of the lymphocytes.

The lymphocyte-containing body fluid is typically blood.

The fluorogenic agent precursor is preferably fluorescein diacetate (FDA).

Typically, in the determination of $K_a$ and $K_b$, physical separation of the fluor-containing lymphocytes from the background material is accomplished by filtration.

Preferably, when exciting the lymphocytes at 470 nm, $\lambda_1$ is 510 nm and $\lambda_2$ is selected to be between 515 nm and 520 nm or 525 nm, typically 515 nm or 525 nm. Alternatively, when exciting the lymphocytes at 442 nm, $\lambda_1$ can be 527 nm and $\lambda_2$ selected to be between 532 nm and 537 nm or 542 nm, typically 532 nm.

An apparatus useful for practicing the method of this invention comprises:

(1) an excitation source for exciting the sample at a selected excitation wavelength;

(2) a fixed polarizer transmitting to the sample only plane-polarized light, the polarizer being disposed between the light source and the sample;

(3) orientation selection means for selectively transmitting plane polarized light in either a first plane parallel to the plane of polarization of the exciting light or a second plane transverse to the first plane, the orientation selection means being disposed in the light path of the fluorescence emitted by the sample;

(4) wavelength selection means for selecting either the primary wavelength, $\lambda_1$ or the secondary wavelength, $\lambda_2$, or subsequent fluorescence emission intensity measurements, the wavelength selection means being disposed in the path of the light emitted from the wavelength selection means;

(5) measuring means for measuring the intensities of the components of the emitted fluorescence polarized in the first and second planes at the wavelength selected by the wavelength selection means; and (6) calculation means for calculating the net polarization value, P, of the fluorescing material in the sample from the measured intensities.

The excitation means can comprise: (1) a light source; and (2) transmission means for transmitting light at a selected excitation wavelength, the transmission means being disposed in the path of the light emitted by the light source.

The fixed polarizer can be arranged to transmit only vertically polarized light to the sample The first and second planes in which the orientation selection means transmits polarized light can then be the vertical and horizontal planes.

The orientation selection means can comprise: (1) a rotatable analyzer disposed in the light path of the fluorescence emitted by the sample; and (2) means for rotating the polarization axis of the analyzer between the first and second planes.

Alternatively, the orientation selection means can comprise: (1) two separate analyzers, a first analyzer with its polarization axis in the first plane and a second analyzer with its polarization axis in the second plane; and (2) analyzer selection means for alternatively positioning the first or the second analyzer in the path of the fluorescence emitted by the sample.

The wavelength selection means can be a single device designed to pass fluorescence emissions alternately at $\lambda_1$ and $\lambda_2$. Preferably, however, the wavelength selection means comprises a pair of emission monochromators or optical filters, one for each wavelength.

When the wavelength selection means comprises a pair of emission monochromators, the apparatus can further comprise:

(1) a pair of photodetectors, one disposed in the exit light path of each of the emission monochromators; and (2) an amplifier to which the outputs from the photodetectors are fed individually. The amplifier includes suitable conventional switching means to select controllably first one and then the other of the photodetector outputs, whereby the selected output is amplified. In this version of the apparatus, the calculation means includes a microprocessor to which the selected output of the amplifier is fed. The microprocessor is programmed to perform the necessary computations to correct for background fluorescence. Preferably, the microprocessor further includes conversion means to convert the output of the amplifier to an equivalent digital representation.

Alternatively, the measuring means can comprise either four separate photodetectors so that a separate photodetector is dedicated to each component of the polarized emitted fluorescence at each wavelength, or a single photodetector.

An alternative version of this apparatus features a rotating polarizer and two fixed analyzers. This version of the apparatus comprises:

(1) an excitation source;

(2) a polarizer disposed between the excitation source and the sample;

(3) a first fixed orientation selection means for selectively transmitting plane-polarized light only in a first plane, the first fixed orientation selection means being disposed in the light path of the fluorescence emitted by the sample;

(4) a second fixed orientation selection means for selectively transmitting plane-polarized light only in a second plane transverse to the first plane, the second fixed orientation selection means being disposed in the light path of the fluorescence emitted by the sample;
(5) a first wavelength selection means for selecting only a primary wavelength, $\lambda_1$, for subsequent fluorescence emission intensity measurements, the first wavelength selection means being disposed in the path of the light emitted from the first fixed orientation selection means;
(6) a second wavelength selection means for selecting only a secondary wavelength, $\lambda_2$, for subsequent fluorescence intensity measurements, the second wavelength selection means being disposed in the path of the light emitted from the second fixed orientation selection means;
(7) measuring means for measuring the intensities of the components of the emitted fluorescence polarized in the first and second planes at the wavelengths selected by the first and second wavelength selection means; and
(8) calculation means for calculating the net polarization value, P, of the fluorescing material in the sample from the measured intensities.

The axis of the rotating polarizer can rotate circularly through an angle of 360° to transmit planepolarized light in all possible orientations to the sample. In this embodiment, the ratio of the polarized fluorescence emission intensity measured in the first plane at $\lambda_1$ to the polarized fluorescence emission intensity measured in the second plane at $\lambda_2$ varies sinusoidally with the rotation of the polarizer through the angle of 360°. Alternatively, the axis of the rotating polarizer can rotate through an angle of 90° and fluorescence intensity measurements can be taken at the extremes of rotation of the polarizer, such that the second plane is orthogonal to the first plane.

Another alternative version of this apparatus measures $I_{tot2}$ directly, eliminating the need for separate measurements of $I_{P2}$ and $I_{T2}$. This alternative version comprises:
(1) an excitation source;
(2) a fixed polarizer;
(3) orientation selection means for selectively transmitting plane polarized light in either a first plane or the second plane, the orientation selection means being movably disposed alternately in the light path of the fluorescence emitted by the sample or outside of the light path;
(4) wavelength selection means;
(5) positioning means interlocked with the wavelength selection means such that the positioning means positions the orientation selection means in the light path only whenever the wavelength selection means selects $\lambda_1$ and positions the orientation selection means outside the light path whenever the wavelength selection means selects $\lambda_2$;
(6) a first measuring means for measuring the intensity of the components of the emitted fluorescence polarized in the first and second planes at $\lambda_1$ whenever the orientation selection means is disposed in the light path;
(7) a second measuring means for measuring $I_{tot2}$, the total intensity of the fluorescence emitted from the sample at $\lambda_2$ whenever the orientation selection means is outside of the light path; and
(8) calculation means.

The orientation selection means can comprise: (1) a rotatable analyzer disposed in the light path of the fluorescence emitted by the sample when the orientation selection means is disposed in the light path; and (2) rotation means.

Alternatively, the orientation selection means can comprise (1) two separate analyzers; and (2) analyzer selection means for alternately positioning the first analyzer or the second analyzer in the light path of the fluorescence emitted by the sample when the orientation selection means is positioned in the light path.

The wavelength selection means can be a single device or a pair of devices, in either case interlocked with the positioning means. The wavelength selection means can be emission monochromators.

When the wavelength selection means are emission monochromators, the first measuring means can comprise a first photodetector disposed in the exit light path of the first emission monochromator and measuring the component of the fluorescence transmitted by the orientation selection means, thereby alternately measuring the component of the fluorescence emissions polarized in the first and second plane at $\lambda_1$. The second measuring means comprises a second photodetector disposed in the exit light path of the second monochromator, and measuring the total intensity of the fluorescence emissions at $\lambda_2$. This embodiment of the apparatus also includes an amplifier as described above, with the calculation means similarly including a microprocessor The microprocessor preferably further includes conversion means to convert the output of the amplifier to an equivalent digital representation.

Another version of the apparatus is similar but includes three photodetectors. In this version, the first measuring means comprises two separate photodetectors:
(1) a first photodetector disposed in the exit light path of the first emission monochromator to which the light transmitted by the orientation selection means when the orientation selection means is in the light path and transmits plane polarized light in the first plane is directed; and
(2) a second photodetector disposed in the exit light path of the first emission monochromator to which the light transmitted by the orientation selection means when the orientation selection means is in the light path and transmits plane polarized light in the second plane is directed. The first photodetector measures the component of the fluorescence emissions polarized in the first plane at $\lambda_1$, while the second photodetector measures the component of the fluorescence emissions polarized in the second plane at $\lambda_1$. In this arrangement, as before, the second measuring means comprises a separate photodetector, here the third photodetector.

Still another basic version of this apparatus makes use of the finding that when the orientation of the polarization axis of the analyzer is at an angle of 54.7° from the plane of polarization of the exciting light, the polarized fluorescence emission intensity measured in this plane at a given wavelength is proportional to the total fluorescence emission intensity at that wavelength, regardless of the degree of polarization of the fluorescence emitted by the sample. When this measurement is made at $\lambda_2$, the measured polarized fluorescence intensity is designated $I_{M2}$ the total fluorescence emission intensity determined therefrom is $I_{tot2}$.

This version of the apparatus comprises:
(1) an excitation source;
(2) a fixed polarizer;
(3) orientation selection means for selectively transmitting plane polarized light in one of three planes:

a vertical plane, a horizontal plane, and a plane oriented 54.7° from the vertical, the orientation selection means disposed in the path of the fluorescence emitted by the sample;

(4) wavelength selection means for selecting either $\lambda_1$ or $\lambda_2$ for subsequent fluorescence emission intensity measurements, the wavelength selection means interlocked with the orientation selection means so that $\lambda_1$ is selected whenever the orientation selection means transmits light in either the vertical plane or the horizontal plane, and so that $\lambda_2$ is selected whenever the orientation selection means transmits light in the plane oriented 54.7° from the vertical;

(5) measuring means for measuring the intensities of the components of the emitted fluorescence polarized in the vertical plane, the horizontal plane, and the plane oriented 54.7° from the vertical, at the wavelength selected by the wavelength selection means; and (6) calculation means for determining $I_{tot2}$ from $I_{M2}$ and calculating P.

The orientation selection means can comprise: (1) a rotatable analyzer; and (2) means for rotating the orientation of the polarization axis of the analyzer between the first, second, and third planes.

Alternatively, the orientation selection means can comprise: (1) three separate analyzers, each with its polarization axis in a different one of the three planes; and (2) analyzer selection means for alternately positioning the first, second, or third analyzer in the path of the fluorescence emitted by the sample.

In this version of the apparatus, the measuring means can comprise a single photodetector, two photodetectors, or three photodetectors. When the wavelength selection means is a pair of emission monochromators, the measuring means can comprise either two or three photodetectors in slightly different arrangements.

When two photodetectors are used, the first photodetector can be disposed in the exit light path of the first emission monochromator and measure alternately the component of the fluorescence transmitted by the orientation selection means in the vertical and the horizontal planes at $\lambda_1$. The second photodetector is disposed in the exit light path of the second emission monochromator and measures the component of the fluorescence transmitted by the orientation selection means whenever the polarization axis of the analyzer is in the plane oriented 54.7° from the vertical.

When three separate photodetectors are used, a single photodetector is dedicated to the measurement of the polarized fluorescence emissions in each of the three planes.

Whether two or three photodetectors are used, the apparatus also further comprises an amplifier as described above, with the calculation means similarly including a microprocessor.

DRAWINGS

These and other features, aspects, and advantages of the present invention will become better understood with reference to the following description, appended claims, and accompanying drawings where:

FIG. 3 is a schematic diagram of a fluorescence spectrophotometer arrangement utilized for measurement of the SCM response of a lymphocyte suspension;

FIG. 4 is a schematic diagram of an alternative fluorescence spectrophotometer arrangement for measurement of the SCM response in which the polarizer rotates and two fixed analyzers are used to transmit the polarized fluorescence emissions from the sample in the first and second planes;

Figure 1:
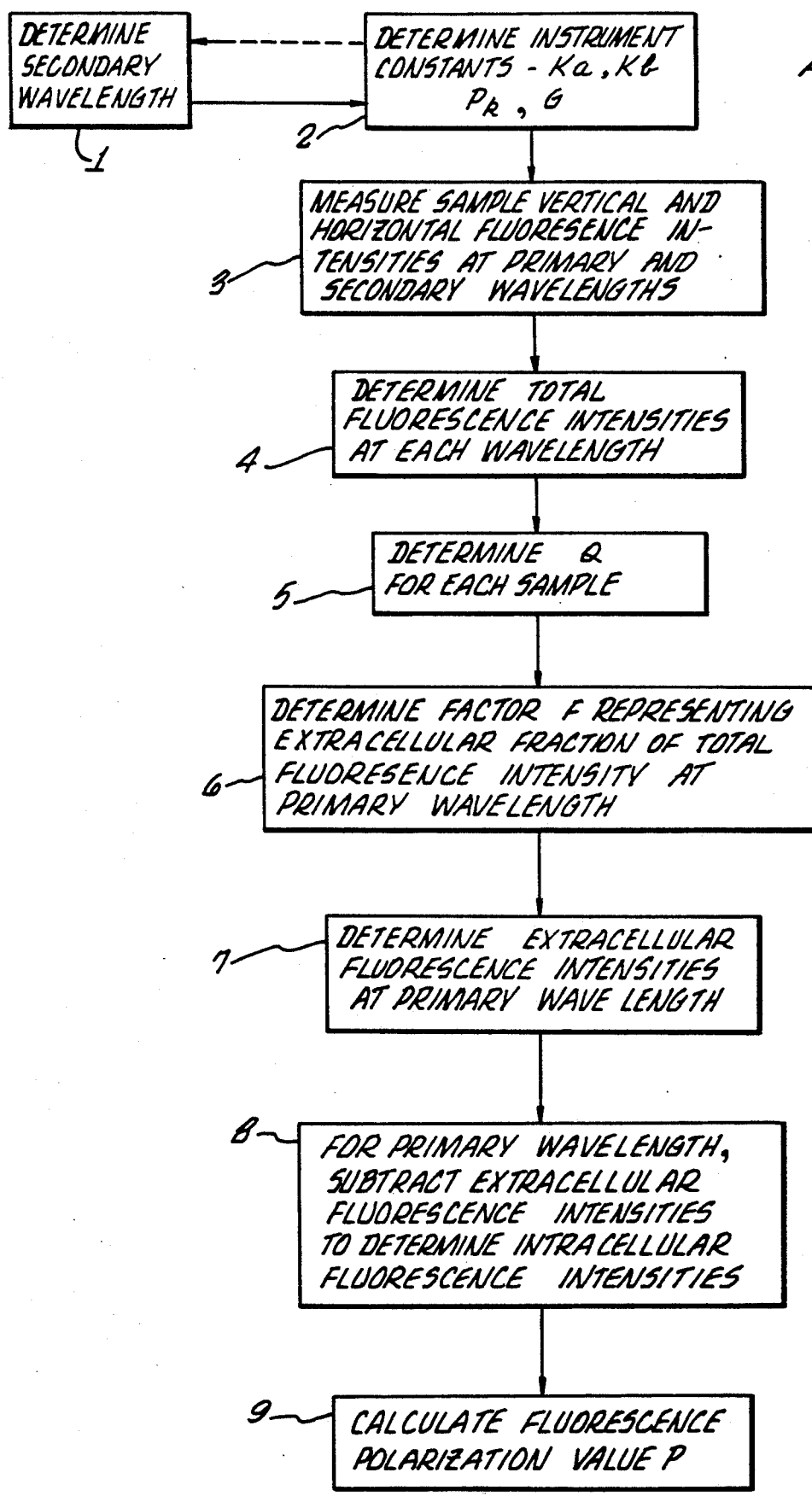
FIG. 1 is a flow chart of a method in accordance with the present invention useful in the general SCM test procedure.

FIG. 5 is a schematic diagram of an alternative fluorescence spectrophotometer arrangement utilized for measurement of the SCM response in which the total fluorescence emission intensity at $\lambda_2$, $I_{tot2}$, is measured directly; and FIG. 6 is a schematic diagram of another alternative fluorescence spectrophotometer arrangement in which the polarized fluorescence emission intensity is also measured at $\lambda_2$ in a plane at an angle 54.7° from the plane of the exciting light, allowing direct calculation of $I_{tot2}$.

DESCRIPTION

This invention relates to methods for correcting fluorescence polarization measurements of suspensions of fluor-containing cells such as lymphocytes for extracellular background fluorescence without filtering the cells from the suspension. The methods are based on the observation that the fluorescence from the fluor-containing cells is bathochromically shifted (shifted to longer wavelengths) relative to the fluorescence from the extracellular background and, therefore the extracellular and the intracellular fluorescence can be regarded as originating from two different fluorophores. The method is not restricted to the analysis of fluorescence emissions from fluor-containing cells in a background of extracellular fluorescence; it is equally applicable to any fluorescent system in which the fluorescence from an environment contributing background fluorescence is shifted in wavelength with respect to the fluorescence from the fluorescing material.

One potential application of the bathochromic shift method of the present invention is in flow cytometry and microscopic observation of single cells. When these techniques are used with fluorescence polarization, a halo is often observed around cells because of concentration gradients in the medium near the cells. This halo effect is enhanced when the permeability of the cell membrane is increased, as when lymphocytes are stimulated by mitogens such as PHA. The method of the present invention can eliminate this halo effect by correcting for the background fluorescence giving rise to it.

Theoretical Background

Fluorescence from intracellular molecules of fluorescein is bathochromically shifted (shifted to longer wavelengths) by about 9 nm relative to the fluorescence from fluorescein in aqueous phosphate buffered saline. The extracellular and intracellular fluorescein fluorescence, therefore, can theoretically be treated as originating from two different fluorophores. On this basis the following mathematical analysis can be applied:

$$I_{tot1} = I_{tot1B} + I_{tot1F} \qquad (1)$$

$$I_{tot2} = I_{tot2B} + I_{tot2F} \quad (2)$$

where:

(a) $I_{tot1}$ is the total intensity of fluorescence at the wavelength $\lambda_1$;

(b) $I_{tot2}$ is the total intensity of fluorescence at the wavelength $\lambda_2$;

(c) $I_{tot1B}$ is the total intensity of fluorescence at the wavelength $\lambda_1$;

(d) $I_{tot2B}$ is the total intensity of fluorescence from the extracellular fluorescein at the wavelength $\lambda_2$;

(e) $I_{tot1F}$ is the total intensity of fluorescence from the intracellular fluorescein at the wavelength $\lambda_1$; and (f) $I_{tot2F}$ is the total intensity of fluorescence from the intracellular fluorescein at the wavelength $\lambda_2$. The term "total" refers to the fluorescence intensity, whether polarized in a particular plane or not. $\lambda_1$ and $\lambda_2$ are two different wavelengths, for example 510 nm and 515 nm respectively. $\lambda_1$ is designated as the first or primary wavelength; all other wavelengths at which measurements are taken, including $\lambda_2$, are designated secondary wavelengths.

In general, the fluor-containing cells subjected to fluorescence polarization are isotropic in their response to polarized light. That is, the degree of polarization of the emitted fluorescence relative to that of the exciting light does not depend on the orientation of the plane-polarized light used to excite the cells. This isotropic response makes the methods described herein applicable whenever the emitted polarized fluorescence is measured in two planes, a first plane and a second plane transverse to the first plane. The fluorescence polarization intensities in these two planes are designated $I_P$ in the first plane and $I_T$ in the second plane. Typically, the first plane is parallel to the plane of polarization of the exciting light, but this is not a requirement for the application of the method. Preferably the two planes are orthogonal.

The fluorescence polarization measuring apparatus used for the methods of this invention uses vertically polarized light to excite the fluor-containing cells and measures the emitted polarized light in the vertical and horizontal planes. Therefore the equations used to define the process of determining fluorescence polarization from these measurements are written in terms of vertically polarized exciting light, with measurements of the emitted polarized light being made in vertical and horizontal planes. In these equations, the vertical plane is the first plane, and the horizontal plane is the second or transverse plane. For simplicity, the intensities in the vertical and horizontal planes will continue to be designated $I_P$ and $I_T$ in the following equations, as this relationship is merely a special case of the more general parallel-transverse relationship of the two planes.

When the SCM test is performed, the total intensity of the fluorescence at a particular wavelength need not necessarily be measured. Rather what can be measured are the intensities of the vertically and the horizontally polarized components of the fluorescence at a particular wavelength. The total fluorescence intensity at a particular wavelength is determined by the equation $$I_{tot1} = I_{P\lambda} + 2(I_{T\lambda} \times G), \quad (3)$$

as previously described in the Summary. Alternatively, only the intensities of the vertically and the horizontally polarized components of the fluorescence at the primary wavelength can be measured, and the apparatus can be arranged to measure the total intensity of the fluorescence at the secondary wavelength. This is feasible because only the total intensity of the fluorescence at the secondary wavelength is actually needed for the performance of the method.

If the following quantities are defined in terms of previously defined quantities:

$$K_a = I_{tot2B}/I_{tot1B}; \quad (4)$$

$$K_b = I_{tot2F}/I_{tot1F}; \text{ and} \quad (5)$$

$$Q = I_{tot2}/I_{tot1}, \quad (6)$$

then the fraction, F, of the total intensity of the fluorescence emissions at the primary wavelength, $\lambda_1$, due to extracellular emissions is given by:

$$F = \frac{K_b - Q}{K_b - K_a}. \quad (7)$$

Once F is determined the vertically and horizontally polarized emission intensities at the primary wavelength due to extracellular fluorescence can be determined by the equations:

$$I_{P1B} = \frac{I_{tot1} \times F}{1 + 2(1 - P_k/1 + P_k)}, \quad (8)$$

and $$I_{T1B} = \frac{I_{tot1} \times F}{(2 + (1 + P_k/1 - P_k)) \times G}, \quad (9)$$

where:

(a) $I_{P1B}$ is the vertically polarized extracellular fluorescence intensity at the primary wavelength $\lambda_1$;

(b) $I_{T1B}$ is the horizontally polarized extracellular fluorescence intensity at the primary wavelength;

(c) $I_{tot1}$ is the total intensity of the fluorescence emissions at the primary wavelength as calculated from equation (3);

(d) F is the fraction of the total intensity of the fluorescence emissions at the primary wavelength due to extracellular fluorescence as calculated from equation (7); and (e) $P_k$ is a constant defined by the relationship:

$$P_k = \frac{I_{P1BS} - G \times I_{T1BS}}{I_{P1BS} + G \times I_{T1BS}}, \quad (10)$$

where:

(i) $I_{P1BS}$ is the vertically polarized fluorescence intensity at the primary wavelength of a separate solution of a nonfluorogenic compound, such as FDA, hydrolyzable intracellularly to a fluorogenic compound, such as fluorescein, from which the lymphocytes have been removed, preferably by filtration;

(ii) $I_{T1BS}$ is the horizontally polarized fluorescence intensity at the primary wavelength of such a separate solution; and (iii) G is the correction factor for the unequal transmission of the vertically and horizontally polarized components of the fluorescence emissions through the optical system of the fluorescence measuring instrument from equation (3). $P_K$ is equivalent to the extracellular fluorescein fluorescence polarization and is a constant equal to 0.0254 at 27° C.

Once $I_{P1B}$ and $I_{T1B}$ are known, the vertically and horizontally polarized emission intensities at the primary wavelength due solely to intracellular fluorescence, $I_{P1F}$ and $I_{T1F}$, can be readily calculated as:

$$I_{P1F} = I_{P1} - I_{P1B} \quad (11)$$

$$I_{T1B} = I_{T1} - I_{T1B}, \quad (12)$$

where $I_{P1}$ and $I_{T1}$ are the polarized fluorescence intensities measured in the first and second planes, respectively, at $\lambda_1$.

Once $I_{P1F}$ and $I_{T1F}$ are known, the net polarization value, P, can be calculated as:

$$P = (I_{P1F} - GXI_{T1F})/(I_{P1F} + GxI_{T1F}). \quad (13)$$

It is the P value that is relevant for the SCM test and whose decrease in response to the challenge of the lymphocytes by an antigen associated with a disease or condition signals a positive response to the SCM test.

It is necessary to determine the constants $K_a$, $K_b$, and $P_k$, as well as G. The first three of these are constants for a particular cell type fluorogenic molecule, and fluorescence measuring instrument. G is constant for a particular fluorescence measuring instrument regardless of the cell type or fluorogenic molecule used. $K_a$, $K_b$, and $P_k$ are all determined by performing the prior art kinetic extrapolation and filtration method on a sample at at least two different wavelengths, one primary wavelength and at least one secondary wavelength, so that the extracellular and intracellular fluorescence intensities at these wavelengths can be determined. G, if not known from previous fluorescence measurements on the same instrument, can be determined from measurements of the vertically and horizontally polarized fluorescence intensities of the filtrate or a solution of the fluorogenic molecule excited with horizontally polarized light.

The process of using the method of the present invention is summarized in the flowchart of FIG. 1 Step 1 is to determine at least one secondary wavelength. Step 2 is to determine the instrument constants $K_a$, $K_b$, and $P_k$, as well as G if not previously determined. Step 3 is to measure the vertically and horizontally polarized fluorescence emission intensities at these same wavelengths—the primary wavelength and at least one secondary wavelength. In step 4, these intensity measurements are then used to determine $I_{total}$ for each wavelength according to equation (3) for each sample. These values of $I_{total}$ at these wavelengths are then used in step 5 to determine a value of Q for each sample according to equation (6). The value of Q varies for each sample according to the relative contributions of intracellular and extracellular fluorescence in that sample, because the intracellular and extracellular fluorescence emissions are regarded as having different spectra. Therefore, the actual fluorescence emission spectrum observed can be regarded as the algebraic superposition of the two spectra, weighted for the relative contributions of each. Q is the only factor varying from sample to sample in a series of measurements on the same cell type using the same intracellular fluorogenic molecule and measured in the same fluorescence measurement apparatus.

Once a value of Q is obtained for each sample, in step 6 this value is used in equation (7) along with $K_a$ and $K_b$ to calculate a value of F for each sample. This value of F is then used in step 7 to determine $I_{P1B}$ and $I_{T1B}$. From these values the vertically and horizontally polarized fluorescence emission intensities at the primary wavelength due to intracellular fluorescence, $I_{P1F}$ and $I_{T1F}$ are then determined in step 8 for each sample In the last step, step 9, these latter values can then be used directly in equation (13) to calculate the net polarization value P for each cell sample.

2. Use of the Bathochromic Shift Method in Performing the SCM Test

Figure 2:
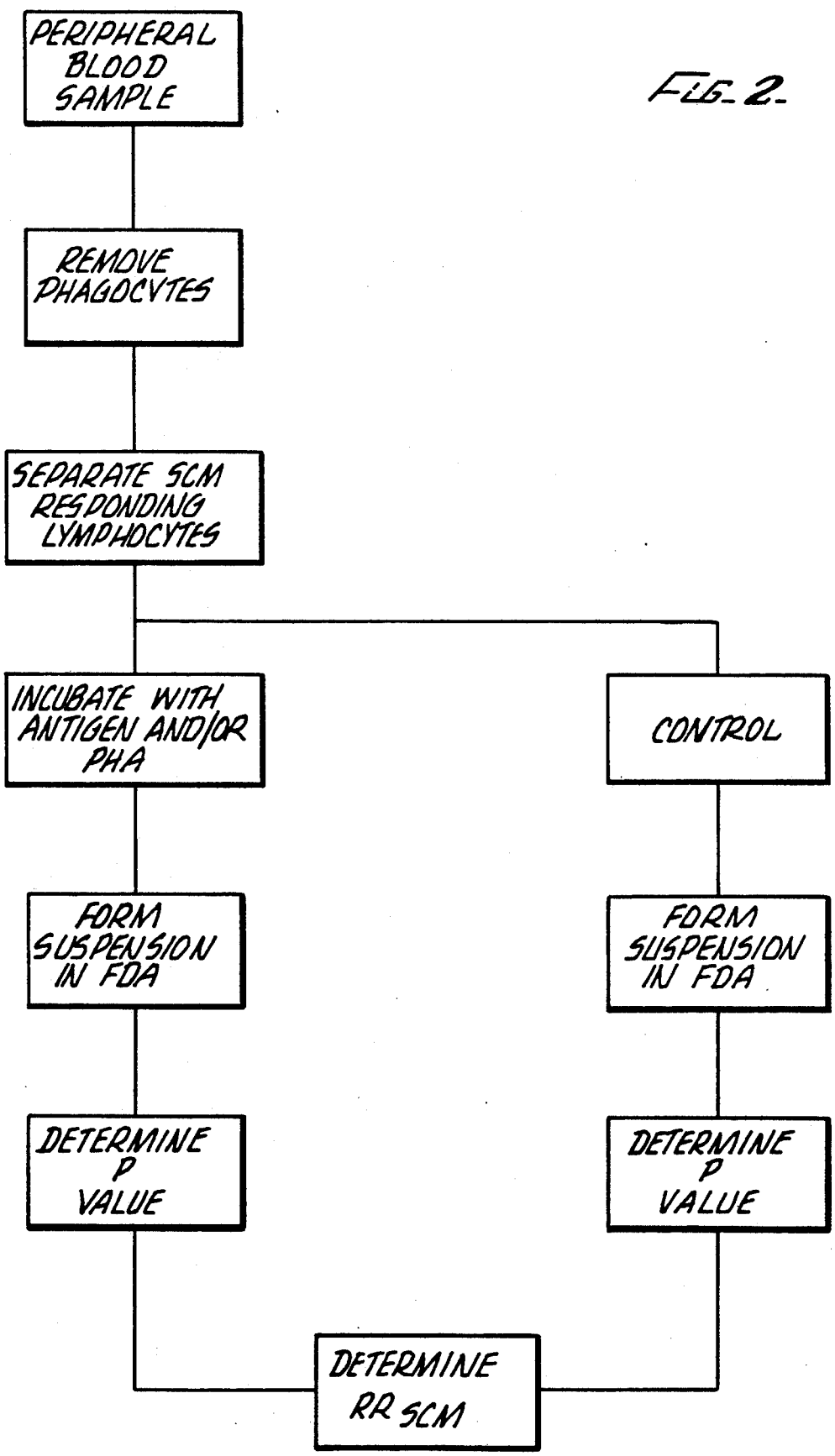
FIG. 2 is a flow chart of the general SCM test procedure as applied in the method of the present invention in FIG. 1.

The general procedure of the SCM test is summarized in the flowchart of FIG. 2.

a. Isolation of Potentially SCM-Responding Lymphocytes

To perform the SCM test, the subpopulation of lymphocytes described as "potentially SCM-responding lymphocytes" is separated from the peripheral blood to be tested. This separation can be performed by the methods described in L. Cercek and B. Cercek, "Application of the Phenomenon of Changes in the Structuredness of Cytoplasmic Matrix (SCM) in the Diagnosis of Malignant Disorders: a Review," *Europ. J. Cancer* 13 903–915 (1977), and in the prior patent application by the Cerceks entitled "Automated Collection of Buoyant Density Specific Cells from Density Gradients," Ser. No. 838,264, filed Mar. 10, 1986, and incorporated herein by this reference. These methods, with reference to FIG. 2, basically involve a first step of removing the phagocytic cells by treating the lymphocytes with iron powder or carbonyl-iron powder and then placing the cells on a magnet to effect separation of the phagocytic cells along with the iron powder from the blood sample. The iron powder separation step can be replaced by other suitable methods of eliminating the phagocytic cells from the blood sample. After the phagocytic cells are removed, the potentially SCM-responding lymphocytes are isolated by centrifuging the lymphocytes through a Ficoll(TM)—Triosil(TM) or Percoll(TM) density gradient solution. The lymphocytes characterized as "potentially SCM-responding lymphocytes" have a buoyant density of about 1.059 g/cm³ to about 1.067 g/cm³ at 20° C. at an osmolality of about 0 315 to about 0.320 Osm/kg. After separation and washing a portion of the potentially SCM-responding lymphocytes is retained as a control and other portions are subsequently stimulated by incubation with a challenging agent such as an antigen derived from or associated with the disease or condition being tested for.

b. General Procedures for Performing the SCM Test

Once the appropriate lymphocytes have been isolated, the SCM test is performed according to the methods described in the *European Journal of Cancer* article, supra. The SCM test measures the decrease in fluorescence polarization after the lymphocytes have been incubated with a challenging agent such as a cancer-associated antigen or an antigen associated with another disease or condition being tested for, or, alternatively, with a mitogen such as phytohaemagglutinin, concanavalin A, or pokeweed mitogen. When the disease to be tested for is cancer, lymphocytes from cancer patients respond with a decrease in the measured fluorescence polarization to cancer-associated antigens and not to mitogens, while lymphocytes from persons free of malignant disease respond only to mitogens and not to the cancer-associated antigens. To compare the response of the lymphocytes to the antigen and to the mitogen, an SCM response ratio, $RR_{SCM}$, can be determined. The $RR_{SCM}$ is defined as:

$$RR_{SCM} = P_\lambda / P_M, \quad (14)$$

where $P_\lambda$ is the net polarization value for the lymphocytes after stimulation with the antigen associated with the disease to be tested for, such as a cancer-associated antigen, and $P_M$ is the net polarization value for another aliquot of the same lymphocytes after stimulation with a mitogen, preferably phytohaemagglutinin PHA).

To ensure the reproducibility of results, using FDA as the fluorogenic agent precursor, the pH of the FDA substrate solution is maintained at or slightly above 7.4 and the osmolality of the solution should be held to within 1% of the isotonic value of 0 330 Osm/kg. The selection of excitation and emission wavelengths is a matter of choice; the optimal wavelength depends on the fluorogenic agent employed. When FDA is used as the fluorogenic agent precursor, good results have been obtained using an excitation wavelength of 470 nm and an emission wavelength of 510 nm. Good results have also been achieved using an excitation wavelength of 442 nm and an emission wavelength of 527 nm using FDA as the fluorogenic agent precursor. Other fluorogenic agent precursors usable include dichlorofluorescein diacetate and trichlorofluorescein diacetate. The fluorogenic agent precursor carboxyfluorescein diacetate does not enter mitochondria, but can be useful for observation of events affecting the SCM and occurring in the cytoplasm or other organelles.

These measurements of the SCM on cell suspensions are conducted in a fluorescence polarization measuring apparatus comprising a fluorescence spectrophotometer equipped with a polarizer designed to pass vertically polarized light between the excitation monochromator or optical filter and the cell sample. The apparatus typically includes a rotatable analyzer capable of passing either vertically or horizontally polarized light between the cell sample and the emission monochromator. Although the spectrophotometer can be equipped with a single photodetector such as a photomultiplier and with means for sequentially measuring the emissions at two different wavelengths, it is preferred that the spectrophotometer be equipped with at least two separate photomultipliers so that emissions at two wavelengths can be measured simultaneously.

3. Apparatus for the SCM Method

Referring to FIG. 3 there is a schematic illustration of one version of an apparatus useful for measuring SCM on cell suspensions in accordance with the method of the invention. The excitation source 10 can comprise a suitable light source such as a xenon lamp as well as a transmission device such as an optical filter or, as shown, an excitation monochromator 12, disposed in the excitation light path of the light source for transmitting light to the sample at a selected excitation wavelength. Alternatively, the excitation source itself can be a source such as a tunable laser adjusted to emit light only at the desired excitation wavelength, in which case the separate transmission device is not needed. In either case, the light is transmitted to a fixed polarizer 14 that transmits only plane-polarized light to the sample cell suspension 16. The sample cell suspension 16 contains intracellularly the fluorogenic compound such as fluorescein produced by hydrolysis of a nonfluorogenic compound such as FDA. Upon exposure to the plane-polarized excitation light the fluorescein molecules fluoresce and the fluorescence emission is directed through an orientation selection device. The orientation selection device can comprise, as shown in FIG. 3, an analyzer 18 fitted with a rotator such as an automatic position changer (not shown) for rotating the orientation of the polarization axis of the analyzer 18 between a first plane parallel to the plane of polarization of the exciting light and a second plane transverse to the first plane, whereby the analyzer 18 alternately transmits the component of the fluorescence emitted by the sample polarized in the first plane and the second plane. Alternatively, the orientation selection device can comprise two separate analyzers and an analyzer selection mechanism for alternately positioning the first analyzer or the second analyzer in the path of the fluorescence emitted by the sample 16. In this arrangement, the first analyzer has its polarization axis in the first plane and the second analyzer has its polarization axis in the second plane. In either case, the fluorescence emission, being divided into these two components, then passes through wavelength selectors such as optical filters, or as illustrated, a pair of emission monochromators 20 and 22, one of which is set to pass only light at the first or primary wavelength, $\lambda_1$, and the other to pass light at the secondary wavelength, $\lambda_2$. A pair of photodetectors 24 and 26, which can be photomultiplier tubes, are placed in the exit light paths of the emission monochromators 20 and 22 respectively. The outputs from the photodetectors 24 and 26 are fed individually to an amplifier 28. The amplifier 28 includes suitable conventional switching devices to select controllably first one and then the other of the photodetector outputs. The selected output is amplified and fed to a suitable microprocessor 30. Preferably, the microprocessor 30 includes circuitry to convert the analog output of the amplifier 28 to an equivalent digital representation. The microprocessor 30 is programmed in an otherwise conventional fashion to perform the necessary mathematical computations to correct for extracellular fluorescence as described above under "Theoretical Background." The output from the microprocessor 30 is then sent to a printer 32 for recording the computed intracellular fluorescein fluorescence polarization values.

An alternative embodiment of the apparatus as shown in FIG. 4 has a rotating polarizer 60 and two fixed analyzers 62 and 64 set to pass light in the first and second planes respectively. The polarizer rotates over 360° to transmit plane-polarized light in all possible orientations to the sample. In this arrangement, the fluorescence emissions passing through the first fixed analyzer 62 then pass through a wavelength selector such as an optical filter, or, as illustrated, an emission monochromator 66 set to pass light only at $\lambda_1$. The polarized fluorescence emissions passing through the second fixed analyzer 64 then pass through an equivalent wavelength selector such as the emission monochromator 68 set to pass light only at $\lambda_2$. The arrangement of the photodetectors 24 and 26, the amplifier 28, the microprocessor 30, and the printer 32 is the same as in the embodiment shown in FIG. 3. In the embodiment with a rotatable polarizer 60, the polarized fluorescence intensities measured by the photodetectors 24 and 26 vary sinusoidally with the rotation of the polarizer 60.

Other alternative embodiments are possible using a rotating polarizer and fixed analyzers. The polarizer need not rotate over a full 360°, but can rotate over any lesser angle. For example, the polarizer can rotate over 90° with measurements being taken at the extremes of rotation of the polarizer. This gives a second plane orthogonal to the first plane.

The fluorescence spectrophotometer utilized has high sensitivity, being capable of detecting fluorescence emissions from a concentration of $10^{-10}$ M fluorescein, and high stability. The spectrophotometer is also able to compensate for fluctuations in the intensity of the excitation light. This compensation ability is important because the intensities of the polarized components of the fluorescence are recorded as a function of time and the bulk concentration of fluorescein in the SCM measurements is only of the order of $10^{-8}$ M to $10^{-9}$ M. Also, instruments employing broad band optical filters or monochromators cannot be used in the SCM measurements since the excitation and emission polarization spectra of the lymphocytes show that changes in the SCM can be detected only within a narrow wavelength region. The spectrophotometer preferably is also fitted with a thermostatically controlled cuvette holder since the fluorescein polarization values are highly temperature dependent, changing by about 3% per degree Celsius change in temperature. Therefore, to ensure the reproducibility of results the temperature of the sample should be closely controlled to plus or minus 0.2° C. The spectrophotometer should have bandwidth and stability characteristics comparable to the Perkin-Elmer model MPF-4 fluorescence spectrophotometer.

Rather than using the pair of photodetectors 24 and 26 for measurement of the vertical and horizontal fluorescence intensity components at the primary wavelength and at a secondary wavelength, as many as four separate photodetectors can be used. This allows a separate photodetector to be dedicated to the horizontally and vertically polarized components of fluorescence at each of the two wavelengths being measured. Alternatively, a single photodetector can be used to measure the horizontally and the vertically polarized components of fluorescence. Also, a single device such as a filter designed to pass fluorescence emissions alternately at the primary wavelength and a secondary wavelength can be employed in place of two filters or monochromators.

Other versions of this apparatus are described below under "Simplification of the Bathochromic Shift Method." These versions can be employed when $I_{tot2}$ is measured directly in place of $I_{P2}$ and $I_{T2}$, or when $I_{tot2}$ is determined directly from measurements made in a third plane oriented 54.7° (the so-called "magic angle") from the orientation of the plane of the polarization of the exciting light such that the intensity of the polarized fluorescence emissions measured in this plane at $\lambda_2$ ($I_{M2}$) is proportional to $I_{tot2}$ regardless of the degree of polarization of the emitted fluorescence.

4. Selection of Wavelengths and Determination of Constants for the Bathochromic Shift Method As outlined in the section entitled "Theoretical Background," the bathochromic shift method of the present invention requires the selection of at least two wavelengths at which the intensity of horizontally and vertically polarized emissions are measured, a primary wavelength and at least one secondary wavelength. The primary wavelength is preferably one of the emission wavelengths in the excitation and emission wavelength combination described above, in the section entitled "General Procedures for Performing the SCM Test." For example, if an excitation wavelength of 470 nm is selected, the primary wavelength, $\lambda_1$, is preferably 510 nm. Similarly, if an excitation wavelength of 442 nm is selected, the primary wavelength is preferably 527 nm. For the purpose of the following description, the excitation-emission wavelength combination of 470 nm and 510 nm is used and the primary wavelength is thus 510 nm.

The secondary wavelength, $\lambda_2$, for fluorescence emission measurement is selected to be within a range of wavelengths relatively close to the primary wavelength, $\lambda_1$. The range of wavelengths is determined by the shift of the fluorescence emission spectrum due to background fluorescence emissions. A secondary wavelength within a range of about 5 nm to about 15 nm above the primary wavelength has been found to produce acceptable results. Once $\lambda_1$ and $\lambda_2$ are decided, $K_a$ and $K_b$ can then be calculated. The constant $K_a$ is obtained by measuring the horizontally and vertically polarized fluorescence intensities at primary and secondary wavelengths of filtrates of SCM-responding lymphocyte suspensions after incubation in the FDA solution. For adequate accuracy, these measurements are repeated many times, preferably times or more. For each set of measurements, the total fluorescence emission intensity is determined at each wavelength by means of equation (2) above. The constant $K_a$ is then obtained as the mean value of the result obtained by dividing the intensity at the secondary wavelength by the intensity at the primary wavelength for each set of measurements. Similarly, the constant $K_b$ is obtained by measuring the horizontally and vertically polarized fluorescence intensities at primary and secondary wavelengths of the SCM-responding lymphocytes themselves after correction for the extracellular background fluorescence. The total fluorescence emission intensity at each wavelength for each set of measurements is then calculated. The constant $K_b$ is then obtained as the mean value of the result obtained by dividing the intensity at the secondary wavelength by the intensity at the primary wavelength for each set of measurements. The constants $K_a$ and $K_b$ are recalculated for each different instrument upon which the method of the present invention is used and for each new fluorogenic agent used in such method.

The secondary wavelength is preferably selected such that the difference between the constants $K_a$ and $K_b$ is maximized. Such a selection process can include, for example, determining $K_a$ and $K_b$ for a plurality of wavelengths between 5 nm and 15 nm above the primary wavelength and selecting the secondary wavelength such that the difference between $K_a$ and $K_b$ has the largest absolute value. Varying the wavelength by, for example, 5 nm during this selection process e.g., 5 nm, 10 nm, and 15 nm) provides suitable resolution for the purpose of selecting the difference between the primary and secondary wavelenqth yielding the largest absolute difference between $K_a$ and $K_b$. As an example, with an excitation wavelength of 470 nm and a primary wavelength of 510 nm, a secondary wavelength of 525 nm was found to give the maximum absolute difference between $K_a$ and $K_b$ and yielded values for $K_a$ and $K_b$ of 1.0393 and 1.2546 respectively. Using the same spectrophotometer, excitation wavelength and primary wavelength, a secondary wavelength of 515 nm, giving a difference between the primary and secondary wavelength of 5 nm, gave a $K_a$ of 1 048 and a $K_b$ of 1.135.

A third constant related to the specific instrument used with the present invention is the extracellular fluorescence polarization value, $P_k$, determined using equation (10). This equation makes use of the vertically and horizontally polarized fluorescence emission intensities measured at the primary wavelength for the filtrate. G is a correction factor for the unequal transmission of the vertically and horizontally polarized components of the fluorescence through the optical measuring system of the fluorescence measuring instrument. The value of G is determined by dividing the intensity of the vertically polarized component of the fluorescence by the intensity of the horizontally polarized component of the fluorescence emitted from either a filtrate solution or a $10^{-7}$ M solution of fluorescein in phosphate buffered saline which has been excited with horizontally polarized light of the same wavelength as the vertically polarized exciting light. For the Perkin-Elmer MPF-4 fluorescence spectrophotometer utilized herein, $G=0.42$. This value of G yields a value for $P_k$ of 0.0254 at 27° C.

With the constants $K_a$, $K_b$, and $P_k$ determined, the background or extracellular fluorescence at the primary wavelength can be determined in accordance with the present invention. These constants can be determined for a particular fluorogenic agent and particular instrument and stored in the instrument for use, as in the automated performance of the method of the present invention. Once these constants are determined, all that the method requires is the measurement of the intensity of the vertically and horizontally polarized components of the fluorescence emissions from the fluor-containing cell sample at the primary wavelength and at least one secondary wavelength. This then allows the ready calculation of the P value for the particular cell sample.

5. Extensions of the Bathochromic Shift Method a. Use of More Than One Secondary Wavelength Although good results are obtained by the use of the bathochromic shift method when fluorescence measurements are made at only one secondary wavelength, greater accuracy can be achieved when fluorescence measurements to compensate for background fluorescence emissions are made at a plurality of secondary wavelengths distributed through a wavelength shift range of about 5 nm to about 15 nm above the primary wavelength. For example, measurements are made not only at the primary wavelength of 510 nm and the first secondary wavelength of 515 nm, but also at additional secondary wavelengths, for example, 518 nm, 522 nm, and 525 nm, distributed throughout the 5 nm to 15 nm wavelength shift range. The additional secondary wavelengths are designated $\lambda_2, \lambda_4, \ldots$.

When a plurality of secondary wavelengths is used, the data analysis method described herein is employed in the same manner as when only one secondary wavelength is used. Equation (7) is used to calculate the factor F for each of the individual secondary wavelengths employed for each sample. The mean value of F for each sample is then determined from the values of F for each of the secondary wavelengths used, and the mean value of F thus determined is then used in equations (8) and (9) to calculate $I_{P1B}$ and $I_{T1B}$. Those values are then used in the rest of the analysis as previously described to determine the polarization values for the samples.

b. Additional Applications of the Method

The bathochromic shift method is not limited to its application to the SCM test with lymphocytes. It can be used in any biological system in which polarized fluorescence is to be measured from cells or other biological structures such as organelles, viruses, or liposomes, in the presence of a background contributing fluorescence. The method as extended has two principal requirements: (1) the fluor used must have distinguishable spectra when incorporated in or bound to the biological structure and when present in the background, and (2) the constants $K_a$, $K_b$, and $P_k$ must be capable of being determined. The determination of these constants can involve physical separation of the biological structure from the background material. This separation can be performed by filtration, as in the application to the SCM test with lymphocytes. Alternately, the separation can be performed by techniques such as centrifugation, gel filtration chromatography, or reversible precipitation of the fluor-containing structures. Also, a measurement of the vertically and horizontally polarized emission intensities at the primary wavelength due solely to the background must be made. This measurement can be made on a filtrate, as in the application of the bathochromic shift method to lymphocytes in the SCM test Equally well, this measurement can be made on a supernatant if the fluor-containing structure is separated out by centrifugation or precipitation.

c. Simplification of the Bathochromic Shift Method

If $K_a$, $K_b$, $P_k$, and G are known, the only use made of the values of $I_{P2}$ and $I_{T2}$, the polarized fluorescence emission intensities measured in the first and second planes at $\lambda_2$, for a particular sample is in the determination of $I_{tot2}$, the total fluorescence intensity at $\lambda_2$. $I_{tot2}$ is then used in the determination of Q and therefore F for that sample. If $I_{tot2}$ is measured or determined directly, there is then no need to measure $I_{P2}$ and $I_{T2}$ separately and the bathochromic shift method of the present invention can be simplified by eliminating the separate measurements of $I_{P2}$ and $I_{T2}$.

(1) Direct Measurement of $I_{tot2}$ $I_{tot2}$ can be measured directly and then used to determine Q and then F using a modification of the fluorescence polarization apparatus previously described. An apparatus suitable for the direct measurement of $I_{tot2}$ as well as $I_{P1}$ and $I_{T1}$ is shown in FIG. 5. This apparatus has an orientation selection device for selectively transmitting plane polarized light in either a first plane parallel to the plane of polarization of the exciting light or a second plane transverse to the first plane. The orientation selection device is movably disposed alternately in the light path of the fluorescence emitted by the cell suspension 16 or outside of the light path. The orientation selection device can comprise a rotatable analyzer 18 and an analyzer rotator 44 for rotating the polarization axis of the analyzer between the two planes. A wavelength selector 40, shown as the pair of emission monochromators 20 and 22, alternately selects $\lambda_1$ or $\lambda_2$. A positioner 42 interlocks with the wavelength selector 40 such that the positioner 42 positions the orientation selection device, including the analyzer 18, within the light path of the fluorescence emitted by the sample only whenever the selector 40 selects $\lambda_1$. The positioner 42 positions the analyzer 18 outside the light path whenever the selector 40 selects $\lambda_2$. When the analyzer 18 is disposed in the light path the analyzer rotator 44 rotates the orientation of the polarization axis of the analyzer 18 between the first plane and the second plane. When the polarization axis of the analyzer 18 is in the first plane, the analyzer transmits $I_{P1}$ for subsequent intensity measurements. When the polarization axis of the analyzer 18 is in the second plane the analyzer transmits $I_{T1}$ for subsequent intensity measurements. When the analyzer 18 is outside of the light path, the apparatus transmits $I_{tot2}$ directly for subsequent measurement.

Alternatively the orientation selection device can comprise two separate analyzers and an analyzer selection mechanism for alternatively positioning the first analyzer or the second analyzer in the light path of the fluorescence emitted by the sample when the orientation selection device is positioned in the light path by the positioner 42. The two analyzers are a first analyzer with its polarization axis in the first plane and a second analyzer with its polarization axis in the second plane.

In this apparatus, the wavelength selector 40 can be a single device interlocked with the analyzer positioner 42 and designed to pass fluorescence emissions alternately at $\lambda_1$ and $\lambda_2$. The selector 40 can also be a pair of devices interlocked with the positioner 42, one device for each wavelength, the first device passing fluorescence emissions at $\lambda_1$ and the second device passing fluorescence emissions at $\lambda_2$. These selectors can be the emission monochromators 20 and 22 of FIG. 5.

In this apparatus, there are two measuring devices. The first measuring device measures only at $\lambda_1$, and the second measuring device measures only at $\lambda_2$. These measuring devices can comprise photodetectors. The first measuring device can comprise either a single photodetector 24 alternately measuring $I_{P1}$ and $I_{T1}$ as shown in FIG. 5, or can comprise a pair of photodetectors measuring $I_{P1}$ and $I_{T1}$ separately. The second measuring device, shown as photodetector 26 in FIG. 5, measures the total intensity of the fluorescence emissions from the sample at $\lambda_2$, $I_{tot2}$.

(2) Determination of $I_{tot2}$ from Measurement of Polarized Fluorescence Emissions at "Magic Angle"

A consequence of the theory of fluorescence polarization is that when measurements are made when the polarization axis of the analyzer is in a plane at an angle of 54.7°, the so-called "magic angle," from the orientation of the plane of polarization of the exciting light, the intensity of the polarized fluorescence so measured is independent of the degree of polarization of the emitted light. See R. D. Spencer & G. Weber, "Influence of Brownian Rotations and Energy Transfer upon the Measurements of Fluorescence Lifetime," *J. Chem. Phys.* 52, 1654–1663 (1970). Accordingly, the intensity of the fluorescence measured at a particular wavelength when the polarization axis of the analyzer is at an angle of 54 7° from the orientation of the plane of polarization of the exciting light is directly proportional to the total intensity of the fluorescence emissions from the sample at that wavelength.

Therefore, the total fluorescence emission intensity at $\lambda_2$ ($I_{tot2}$) can be determined by measurement of the polarized fluorescence intensity at the "magic angle" ($I_{M2}$) as long as the proportionality constant is known. This proportionality constant can be determined by measurement of $I_{tot2}$ and $I_{M2}$ for one sample, and remains constant for a given instrument and $\lambda_2$.

This procedure can be used regardless of the orientation of the plane of polarization of the exciting light and of the first and second planes of polarization of the emitted fluorescence in which intensity measurements are made.

An apparatus suitable for the determination of $I_{tot2}$ from $I_{M2}$ is shown in FIG. 6. This apparatus has an orientation selection device for selectively transmitting plane polarized light in one of three planes: (1) a vertical plane; (2) a horizontal plane; and (3) a plane oriented 54.7° from the vertical. The orientation selection device is disposed in the path of the fluorescence emitted by the cell suspension 16. The orientation selection device can comprise, as shown in FIG. 6, a rotatable analyzer 18 always disposed in the light path of the fluorescence emitted by the cell suspension 16, and an analyzer rotator 44 rotating the orientation of the polarization axis of the analyzer 18. A wavelength selector 40, shown as the pair of monochromators 20 and 22, can select either $\lambda_1$ or $\lambda_2$. The wavelength selector 40 is interlocked with the analyzer rotator 44 so that $\lambda_1$ is selected whenever the orientation of the polarization axis of the analyzer 18 is in either the vertical plane or the horizontal plane. The selector 40 selects the secondary wavelength $\lambda_2$ only when the orientation of the polarization axis is in the plane 54.7° from the vertical. The selector 40 can comprise a single device designed to pass fluorescence emissions alternately at $\lambda_1$ and $\lambda_2$. Alternatively, the selector 40 can comprise a pair of devices each interlocked with the analyzer rotator 44. If a pair of devices is used, there is one device for each wavelength, the first device selecting $\lambda_1$ and the second device selecting $\lambda_2$. These devices can be the emission monochromators 20 and 22 of FIG. 6.

Alternatively, the orientation selection means can comprise three separate analyzers, one with its polarization axis in each plane, and an analyzer selection mechanism for alternately positioning each of the three analyzers in the path of the fluorescence emitted by the cell suspension 16.

The apparatus further comprises a measuring device or devices for measuring the intensities of the components of the emitted fluorescence polarized in the three planes at the wavelength selected by the wavelength selector 40. Several arrangements of the measuring device or devices are possible The measuring device can comprise a single photodetector alternately measuring $I_{P1}$, $I_{T1}$, and $I_{M2}$. Alternatively, the measuring devices can also comprise two or three photodetectors. When the wavelength selector 40 comprises two emission monochromators 20 and 22, as shown in FIG. 6, and the measuring devices comprise two photodetectors 24 and 26, the photodetectors are: (1) a first photodetector 24 disposed in the exit light path of the first emission monochromator 20 and measuring alternately the components of the fluorescence transmitted by the analyzer in the vertical and horizontal planes at $\lambda_1$ ($I_{P1}$ and $I_{T1}$); and (2) a second photodetector 26 disposed in the exit light path of the second monochromator 22 and measuring the component of the fluorescence transmitted by the analyzer 18 whenever the polarization axis of the analyzer 18 is in the plane 54.7° from the vertical ($I_{M2}$). The measuring devices can also comprise three separate photodetectors. When the wavelength selector 40 comprises two emission monochromators 20 and 22, two of the photodetectors can be disposed in the exit light path of the first emission monochromator 20, the first photodetector measuring $I_{P1}$ and the second measuring $I_{T1}$. The third photodetector is disposed in the exit light path of the second emission monochromator 22 and measures $I_{M2}$.

In any version of the apparatus designed to measure $I_{M2}$ the calculation device, such as the microprocessor 30, necessarily includes circuitry for determining $I_{tot2}$ from $I_{M2}$. The proportionality constant between $I_{M2}$ and $I_{tot2}$ can be determined by prior measurements and supplied to the calculation device for storage within the calculation device.

EXAMPLE

Potentially SCM-responding lymphocytes were separated from samples of peripheral blood of donors, both donors free of malignancy and donors with cancer, in accordance with the method described in the *European Journal of Cancer* article by L. Cercek and B. Cercek. Samples of peripheral blood from which the phagocytes had been removed were layered on a Ficoll-Triosil density gradient solution having a density of 1.081 g/cm$^3$ at 25° C. and an osmolality of 0.320 Osm/kg, followed by centrifugation at 550×g at 20° C. In accordance with the SCM procedure for cancer testing, an aliquot of each sample of these lymphocytes was exposed to phytohaemagglutinin (PHA) and a second aliquot of each sample was exposed to an extract comprising pooled proteins from a variety of malignant tissues, referred to as cancer basic protein (CaBP). CaBP is a basic protein or group of similar basic proteins which is an effective challenging agent for lymphocytes from donors with cancer in the SCM test, but causes no response in the SCM test when used as the challenging agent for lymphocytes from donors free of cancer in the SCM test. In accordance with our test method the ratio of the net polarization value, $P_{CaBP}$, for an aliquot of lymphocytes incubated with CaBP to the net polarization value, $P_{PHA}$, for an aliquot of lymphocytes from the same donor incubated with PHA is an indication of the presence or absence of cancer in the donor. This ratio is referred to as the SCM response ratio or $RR_{SCM}$, in terms of the challenging agents used:

$$RR_{SCM} = P_{CaBP}/P_{PHA}$$

This ratio has been found to be about 1.1 to about 1.8 in healthy donors as compared to about 0.5 to about 0.95 in donors afflicted with malignant disorders.

After incubation with either CaBP or PHA and formation of the lymphocyte-FDA suspensions in accordance with the method described in the *European Journal of Cancer* article cited above, polarization values for the lymphocyte suspensions with each challenging agent were determined by the previously published method in which the horizontally and vertically polarized components of the fluorescence emissions were measured at a single emission wavelength, 510 nm, using an excitation wavelength of 470 nm. The measurements were made on a Perkin-Elmer fluorescence spectrophotometer model MPF-4.

The horizontally and vertically polarized components of the fluorescence emissions were then measured at a second emission wavelength, 515 nm. The samples were then filtered as described in the previously published method, and the horizontally and vertically polarized components of the fluorescence emissions were then measured from the filtrate at an excitation wavelength of 470 nm and an emission wavelength of 510 nm.

From these measurements, two separate sets of calculations were made: (1) calculations of the $P_{CaBP}$ and $P_{PHA}$ from the fluorescence emissions at 510 nm from the cell suspension and the filtrate according to the previously published method; and (2) calculations of the $P_{CaBP}$ and the $P_{PHA}$ from the fluorescence emissions at 510 nm and 515 nm from only the cell suspension, according to the method of the present invention, treating 510 nm as the primary wavelength, $\lambda_1$, and 515 nm as the secondary wavelength, $\lambda_2$. From each of these sets of calculations of $P_{CaBP}$ and $P_{PHA}$, an $RR_{SCM}$ value was determined. These results are shown in Table 1.

Table 1 shows that the agreement between the RRSCM as calculated by the previously published filtration method and as calculated by the bathochromic shift method of the present invention is quite good and is within acceptable limits of accuracy as predicted by an error propagation analysis. These results show that samples 1–5 have SCM response ratios of approximately 1.15 and above indicating an absence of cancer in the donor, while the SCM response ratios for samples 6–9 are all well below 1.0 indicating that the donor is afflicted with cancer. These results obtained by the SCM test were confirmed by actual diagnosis.

The method of measuring fluorescence polarization of the present invention achieves the goals which have been sought, and possesses a number of significant advantages over the previously-described filtration method. The method is rapid, as all that is done is the measurement of the polarized fluorescence emissions at two wavelengths. There is no need to measure the fluorescence polarization over an extended period of time, such as four to seven minutes, as previously done. The method is suitable for automation, as the fluorescence spectrophotometer can be programmed with the necessary constants for calculation according to the method. The method requires only a small sample, as there is no need to recover a filtrate from each sample. The method requires only a fluorescence spectrophotometer. Even if the spectrophotometer is not automated, it is far less difficult to readjust the wavelength and make two measurements on each sample than to perform the previous filtration method on each sample, and the worker performing the measurements needs less specialized training than with the previous filtration technique. The method is suitable for the processing of a large number of samples. Most importantly, the method eliminates the high and variable backgrounds often observed with the filtration method.

Although the present invention has been described in considerable detail with regard to certain preferred versions thereof, other versions are possible Therefore, the spirit and scope of the appended claims should not be limited to the description of the preferred versions contained therein.

TABLE 1

COMPARISON OF FILTRATION AND BATHOCHROMIC SHIFT METHODS FOR DETERMINATION OF $RR_{SCM}$

| Sample No. | Challenging Agent | P | | $RR_{SCM}$ | |
|---|---|---|---|---|---|
| | | Filtration Method | Shift Method | Filtration Method | Shift Method |
| 1 | PHA[a] | 0.154 | 0.128 | 1.36 | 1.41 |
| | CaBP[b] | 0.210 | 0.180 | | |
| 2 | PHA | 0.137 | 0.122 | 1.42 | 1.55 |
| | CaBP | 0.195 | 0.189 | | |

TABLE 1-continued

COMPARISON OF FILTRATION AND BATHOCHROMIC SHIFT METHODS FOR DETERMINATION OF $RR_{SCM}$

| Sample No. | Challenging Agent | P Filtration Method | P Shift Method | $RR_{SCM}^c$ Filtration Method | $RR_{SCM}^c$ Shift Method |
|---|---|---|---|---|---|
| 3 | PHA | 0.140 | 0.133 | 1.39 | 1.35 |
|   | CaBP | 0.195 | 0.189 |   |   |
| 4 | PHA | 0.163 | 0.161 | 1.28 | 1.14 |
|   | CaBP | 0.208 | 0.183 |   |   |
| 5 | PHA | 0.145 | 0.170 | 1.39 | 1.27 |
|   | CaBP | 0.202 | 0.215 |   |   |
| 6 | PHA | 0.201 | 0.215 | 0.76 | 0.74 |
|   | CaBP | 0.152 | 0.160 |   |   |
| 7 | PHA | 0.202 | 0.208 | 0.78 | 0.79 |
|   | CaBP | 0.158 | 0.164 |   |   |
| 8 | PHA | 0.202 | 0.196 | 0.80 | 0.84 |
|   | CaBP | 0.161 | 0.164 |   |   |

Samples 1-5 were from donors free of malignancy; samples 6-8 were from donors with cancer.
[a]PHA is phytohaemagglutinin
[b]CaBP is cancer basic protein
[c]$RR_{SCM}$ is the P value for CaBP divided by the P value for PHA

What is claimed is:

1. A method of measuring polarized fluorescent emissions from a fluorescent material in a sample comprising the fluorescing material and a background material, the background material contributing background fluorescence, where the emissions spectrum of the background fluorescence is shifted relative to the emissions spectrum of the fluorescing material, while compensating for the background fluorescence without separating the fluorescing material from the background material of each sample, the method comprising the steps of:
    (a) exciting the sample with plane-polarized light;
    (b) measuring the polarized fluorescence emissions from the sample at a primary wavelength ($\lambda_1$), the measurements being made in two planes, a first plane and a second plane transverse to the first plane, the measurements yielding:
        (i) the measured fluorescence intensity in the first plane at $\lambda_1$ ($I_{P1}$); and
        (ii) the measured fluorescence intensity in the second plane at $\lambda_1$ ($I_{T1}$);
    (c) determining at a secondary wavelength ($\lambda_2$), different from $\lambda_1$, and within the range of wavelengths determined by the measured shift of the fluorescence emissions spectrum due to background fluorescence emissions, the total intensity of the fluorescence ($I_{tot2}$);
    (d) determining from $I_{P1}$, $I_{T1}$, and $I_{tot2}$, the polarized fluorescence emission intensity in the first plane ($I_{P1B}$) and the second plane ($I_{T1B}$) emitted by the background material at $\lambda_1$; and
    (e) subtracting $I_{P1B}$ from $I_{P1}$ to obtain a first value ($I_{P1F}$) and subtracting $I_{T1B}$ from $I_{T1}$ to obtain a second value ($I_{T1F}$), where $I_{P1F}$ and $I_{T1F}$ are the emission intensities at $\lambda_1$ in the first and second planes due solely to the fluorescing material.

2. The method of claim 1 wherein the first plane is parallel to the plane of polarization of the exciting light.

3. A method of measuring polarized fluorescence emissions from a fluorescing material in a sample comprising the fluorescing material and a background material the background material contributing background fluorescence, where the emission spectrum of the background fluorescence is shifted relative to the emission spectrum of the fluorescing material, while compensating for the background fluorescence without separating the fluorescing material from the background material of each sample, the method comprising the steps of:
    (a) exciting the sample with plane-polarized light;
    (b) measuring the polarized emissions from the sample at a primary wavelength ($\lambda_1$) and a secondary wavelength ($\lambda_2$) different from $\lambda_1$ and within the range of wavelengths determined by the measured shift of the fluorescence spectrum due to background fluorescence emissions, the measurements for each wavelength being made in two planes, a first plane and second plane transverse to the first plane, the measurements yielding:
        (i) the measured fluorescence intensity in the first plane at $\lambda_1$ ($I_{P1}$);
        (ii) the measured fluorescence intensity in the second plane at $\lambda_2$ ($I_{P2}$);
        (iii) the measured fluorescence intensity in the second plane at $\lambda_1$ ($I_{T1}$); and
        (iv) the measured fluorescence intensity in the second plane at $\lambda_2$ ($I_{T2}$);
    (c) determining from $I_{P1}$, $I_{P2}$, $I_{T1}$, and $T_{T2}$ the polarized fluorescence emission intensities in the first plane ($I_{P1B}$) and the second plane ($I_{T1B}$) emitted by the background material at $\lambda_1$; and
    (d) subtracting $I_{P1B}$ from $I_{P1}$ to obtain a first value ($I_{T1F}$) and subtracting $I_{T1F}$ from $I_{T1}$ to obtain a second value ($I_{T1F}$), where $I_{P1F}$ and $I_{T1F}$ are the emission intensities at $\lambda_1$ in the first and second planes due solely to the fluorescing material.

4. The method of claim 3 wherein the first plane is parallel to the plane of polarization of the exciting light.

5. A method of measuring polarized fluorescence emissions from a fluorescing material in a sample comprising the fluorescing material and a background material, the background material contributing background fluorescence, where the emission spectrum of the background fluorescence is shifted relative to the emission spectrum of the fluorescing material, while compensating for the background fluorescence without separating the fluorescing material from the background material of each sample, the method comprising the steps of:
    (a) exciting the sample with plane-polarized light;
    (b) measuring the polarized fluorescence emissions from the sample at a primary wavelength ($\lambda_1$), the measurements being made in two planes, a first plane and a second plane transverse to the first plane, the measurements yielding;
        (i) the measured fluorescence intensity in the first plane at $\lambda_1$ ($I_{P1}$); and
        (ii) the measured fluorescence intensity in the second plane at $\lambda_1$ ($I_{T1}$);
    (c) measuring directly at a secondary wavelength ($\lambda_2$) different from $\lambda_1$ and within the range of wavelengths determined by the measured shift of the fluorescence emission spectrum due to background fluorescence emissions, the total intensity of the fluorescence emissions ($I_{tot2}$);
    (d) determining from $I_{P1}$, $I_{T1}$, and $I_{tot2}$ the polarized fluorescence emission intensities in the first plane ($I_{P1B}$) and the second plane ($I_{T1B}$) emitted by the background material at $\lambda_1$; and
    (e) subtracting $I_{P1B}$ from $I_{P1}$ to obtain a first value ($I_{P1F}$) and subtracting $I_{T1B}$ from $I_{T1}$ to obtain a second value ($I_{T1F}$), where $I_{P1F}$ and $I_{T1F}$ are the emission intensities at $\lambda_1$ in the first and second planes due solely to the fluorescing material.

6. The method of claim 5 wherein the first plane is parallel to the plane of polarization of the exciting light.

7. A method of measuring polarized fluorescence emissions from a fluorescing material in a sample comprising the fluorescing material and a background material, the background material contributing background fluorescence, where the emission spectrum of the background fluorescence is shifted relative to the emission spectrum of the fluorescing material, while compensating for the background fluorescence without separating the fluorescing material from the background material of each sample, the method comprising the steps of:

(a) exciting the sample with plane-polarized light;

(b) measuring the polarized fluorescence emissions from the sample at a primary wavelength ($\lambda_1$), the measurements being made in two planes, a first plane and a second plane transverse to the first plane, the measurements yielding:
  (i) the measured fluorescence intensity in the first plane at $\lambda_1$ ($I_{P1}$); and
  (ii) the measured fluorescence intensity in the second plane at $\lambda_1$ ($I_{T1}$);

(c) measuring at a secondary wavelength ($\lambda_2$) different from $\lambda_1$ and within the range of wavelengths determined by the measured shift of the fluorescence emission spectrum due to background fluorescence emissions, and in a plane oriented 54.7° from the plane of the exciting light, the fluorescence emission intensity in the plane at $\lambda_2$ ($I_{M2}$), whereby the value of $I_{M2}$ is proportional to the total fluorescence emission intensity at $\lambda_2$ ($I_{tot2}$) regardless of the degree of polarization of the fluorescence emitted by the sample;

(d) determining $I_{tot2}$ from $I_{M2}$;

(e) determining from $I_{P1}$, $I_{T1}$, and $I_{tot2}$ the polarized fluorescence emission intensities in the first plane ($I_{P1B}$), and the second plane ($I_{T1B}$) emitted by the background material at $\lambda_2$; and (f) subtracting $I_{P1B}$ from $I_{P1}$ to obtain a first value ($I_{P1F}$) and subtracting $I_{T1B}$ from $I_{T1}$ to obtain a second value ($I_{T1F}$), where $I_{P1F}$ and $I_{T1F}$ are the emission intensities at $\lambda_1$ in the first and second planes due solely to the fluorescing material.

8. The method of claim 7 wherein the first plane is parallel to the plane of the exciting light.

9. The method of claim 4 wherein the first and second planes are orthogonal.

10. The method of claim 6 wherein the first and second planes are orthogonal.

11. The method of claim 8 wherein the first and second planes are orthogonal.

12. The method of claim 9 wherein the exciting plane-polarized light is vertically polarized and the vertically and horizontally polarized fluorescence emissions from the sample are measured.

13. The method of claim 10 wherein the exciting plane-polarized light is vertically polarized and the vertically and horizontally polarized fluorescence emissions from the sample are measured.

14. The method of claim 11 wherein the exciting plane-polarized light is vertically polarized and the vertically and horizontally polarized fluorescence emissions from the sample are measured.

15. The method of claim 1, 3, 5, or 7 wherein $\lambda_2$ is selected so that the absolute value of $((I_{tot1F}/I_{tot1B}) - (I_{tot2F}/I_{tot2B}))$ is maximized where $I_{tot1F}$ and $I_{tot2F}$ are the total fluorescence emission intensities from the fluorescing material at $\lambda_1$ and $\lambda_2$ respectively, and where $I_{tot1B}$ and $I_{tot2B}$ are the total fluorescence emission intensities from the background material at $\lambda_1$ and $\lambda_2$ respectively.

16. The method of claim 1, 3, 5, or 7 wherein the difference between $\lambda_1$ and $\lambda_2$ is at least about 5 nm.

17. The method of claim 1, 3, 5, or 7 wherein the difference between $\lambda_1$, and $\lambda_2$ is no greater than about 15 nm.

18. The method of claim 1, 3, 5, or 7 wherein there is only one $\lambda_2$.

19. The method of claim 1, 3, 5, or 7 wherein $\lambda_1$ is at the maximum of the fluorescence emission spectrum of the fluorescing material.

20. The method of claim 9, 10, or 11 further comprising the step of determining the net polarization value, P, of the fluorescing material from $I_{P1F}$ and $I_{T1F}$.

21. The method of claim 12 wherein the determination of $I_{P1B}$ and $I_{T1B}$ comprises:

(a) obtaining from $I_{P1}$, $I_{T1}$, $I_{P2}$, and $I_{T2}$ the total fluorescence emissions of the sample at $\lambda_1$ and $\lambda_2$, $I_{tot1}$ and $I_{tot2}$, in accordance with the following relationship:

$$I_{tot\lambda} = I_{P\lambda} + 2(I_{T\lambda} \times G),$$

wherein $I_{tot\lambda}$ is the total intensity of the fluorescence emissions from the sample at the wavelength $\lambda$, with $\lambda$ being equal to $\lambda_1$ or $\lambda_2$, $I_{P\lambda}$ and $I_{T\lambda}$ are either $I_{P1}$ and $I_{T1}$ or $I_{P2}$ and $I_{T2}$ depending upon the value of $\lambda$ chosen, and G is a correction factor of the unequal transmission of the vertically and horizontally polarized fluorescence emissions through the optical system of a fluorescence measuring instrument;

(b) determining a factor F representing the fraction of the total intensity of the fluorescence emissions at $\lambda_1$ due to background fluorescence by the relationship:

$$F = \frac{K_b - Q}{K_b - K_a},$$

wherein:
(i) $K_a$ is a ratio obtained by dividing the total fluorescence emission intensity for the background material at $\lambda_2$, $I_{tot2B}$, by the total fluorescence intensity for the background material at $\lambda_1$, $I_{tot1B}$;
(ii) $K_b$ is a ratio obtained by dividing the total fluorescence emission intensity for the fluorescing material at $\lambda_2$, $I_{tot2}$, by the total fluorescence emission intensity for the fluorescing material at $\lambda_1$, $I_{tot\lambda1F}$, the determination of $K_a$ and $K_b$ requiring separation of the fluorescing material and the background material, the determination of $K_a$ and $K_b$ being made for at least one sample separate from the sample on which the measurement of polarized fluorescence emissions is made, $K_a$ and $K_b$ being constants for the particular instrumentation used; and
(iii) Q is the ratio of $I_{tot2}$ divided by $I_{tot2}$, Q varying with the relative contributions to fluorescence of the fluorescing material and the background material; and (c) determining from the factor F the values of $I_{P1B}$ and $I_{T1B}$ according to the relationships:

$$I_{P1B} = \frac{I_{tot1} \times F}{1 + 2(1 - P_k/1 + P_k)},$$

and

-continued $$I_{T1B} = \frac{I_{tot1} \times F}{(2 + (1 + P_k/1 - P_k)) \times G},$$

where $P_k$ is a constant defined by the relationship:

$$P_k = \frac{I_{P1BS} - G \times I_{T1BS}}{I_{P1BS} + G \times I_{T1BS}},$$

wherein $I_{P1BS}$ and $I_{T1BS}$ are the vertically and horizontally polarized fluorescence emission intensities, respectively, at $\lambda_1$, of the background material in a separate sample from which the fluorescing material has been removed, and G is a correction factor for the unequal transmission of the vertically and the horizontally polarized fluorescence emissions through the optical system of a fluorescence measuring instrument.

22. The method of claim 21 further comprising the steps of:
   (a) determining the following at a second secondary wavelength, $\lambda_3$, within the range of wavelengths determined by the shift of the fluorescence emission spectrum due to background fluorescence emissions:
      (i) the vertically and horizontally polarized fluorescence emissions from the sample $I_{P3}$ and $I_{T3}$;
      (ii) the total fluorescence emission intensity from the background material, $I_{tot3B}$, the fluorescing material having been removed from the sample; and
      (iii) the total fluorescence emission intensity from the fluorescing material, $I_{tot3F}$;
   (b) determining from $I_{P3}$, $I_{T3}$, $I_{tot3B}$, $I_{tot3F}$, $I_{P1}$, $I_{T1}$, $I_{tot1B}$, and $I_{tot1F}$ a second value of the factor F, $F_2$;
   (c) determining the average value, $F_{av}$, of the factor F, from the first value of F, $F_1$, determined at $\lambda_1$ and $\lambda_2$, and from $F_2$; and
   (d) using $F_{av}$ in determining $I_{P1B}$ and $I_{T1B}$.

23. The method of claim 1, 3, 5, or 7 wherein the fluorescing material is fluorescing cells.

24. A method for determining the net polarization value, P, or lymphocytes in a suspension of a fluorogenic agent precursor, where there is a background of extracellular fluorescence such that the spectrum of the fluorescent emissions attributable to the extracellular background is shifted relative to the spectrum of the fluorescence emissions attributable to the lymphocytes, the method comprising the steps of:
   (a) exciting the lymphocytes with plane-polarized light;
   (b) measuring the polarized emissions from the suspension at a primary wavelength ($\lambda_1$) and a secondary wavelength ($\lambda_2$) different from $\lambda_1$ and within the range of wavelength determined by the measured shift of the fluorescence emissions spectrum due to background fluorescence emissions, the measurements for each wavelength being made in two planes, a first plane parallel to the plane of polarization of the exciting light and a second plane transverse to the first plane, the measurements yielding;
      (i) the measured fluorescence intensity in the first plane at $\lambda_1$ ($I_{P1}$);
      (ii) the measured fluorescence intensity in the second plane at $\lambda_2$ ($I_{P2}$);
      (iii) the measured fluorescence intensity in the second plane at $\lambda_1$ ($I_{T1}$); and
      (iv) the measured fluorescence intensity in the second plane at $\lambda_2$ ($I_{T2}$);
   (c) determining from $I_{P1}$, $I_{P2}$, $I_{T1}$, and $I_{T2}$ the polarized fluorescence emission intensities in the first plane ($I_{P1B}$) and the second plane ($I_{T1B}$) emitted by the extracellular background material at $\lambda_1$; and
   (d) subtracting $I_{P1B}$ from $I_{P1}$ to obtain a first value ($I_{P1F}$) and subtracting $I_{T1B}$ from $I_{T1}$ to obtain a second value ($I_{T1F}$), and emission intensities at $\lambda_1$ in the first and second planes attributable to intracellular fluorescence from the lymphocytes; and
   (e) determining P from $I_{P1F}$ and $I_{T1F}$.

25. A method for determining the net polarization value, P, of lymphocytes in a suspension of a fluorogenic agent precursor, where there is a background of extracellular florescence such that the spectrum of the fluorescence emissions attributable to the extracellular background is shifted relative to the spectrum of the fluorescence emissions attributable to the lymphocytes, the method comprising the steps of:
   (a) exciting the lymphocytes with plane-polarized light;
   (b) measuring the polarized fluorescence emissions from the sample at a primary wavelength ($\lambda_1$), the measurements being made in two planes, a first plane parallel to the plane of polarization of the exciting light and a second plane transverse to the first plane, the measurements yielding:
      (i) the measured fluorescence intensity in the first plane at $\lambda_1$ ($I_{P1}$); and
      (ii) the measured fluorescence intensity in the second plane at $\lambda_1$ ($I_{T1}$);
   (c) measuring at a secondary wavelength ($\lambda_2$) different from $\lambda_1$ and within the measured range of wavelengths determined by the shift of emissions spectrum due to background fluorescence emissions, the total intensity of the fluorescence emissions ($I_{tot2}$);
   (d) determining from $I_{P1}$, $I_{T1}$, and $I_{tot2}$ the polarized fluorescence emission intensities in the first plane ($I_{P1B}$) and the second plane ($I_{T1B}$) emitted by the extracellular background material at $\lambda_1$;
   (e) subtracting $I_{P1B}$ from $I_{P1}$ to obtain a first value ($I_{P1F}$) and subtracting $I_{T1B}$ from $I_{T1}$ obtain a second value ($I_{T1F}$), the emission intensities at $\lambda_1$ in the first and second planes attributable to intracellular fluorescence from the lymphocytes; and
   (f) determining P from $I_{P1F}$ and $I_{T1F}$.

26. A method for determining the net polarization value, P, of lymphocytes in a suspension of a fluorogenic agent precursor, where there is a background of extracellular fluorescence such that the spectrum of the fluorescence emissions attributable to the extracellular background is shifted relative to the spectrum of the fluorescence emissions attributable to the lymphocytes, the method comprising the steps of:
   (a) exciting the lymphocytes with plane-polarized light;
   (b) measuring the polarized fluorescence emissions from the suspension at a primary wavelength ($\lambda_1$), the measurements being made in two planes, a first plane parallel to the plane of polarization of the exciting light and a second plane transverse to the first plane, the measurements yielding:
      (i) the measured fluorescence intensity in the first plane at $\lambda_1$ ($I_{P1}$); and (ii) the measured fluorescence intensity in the second plane at $\lambda_1$ ($I_{T1}$);

(c) measuring at a secondary wavelength ($\lambda_2$) different from $\lambda_1$ and within the range of wavelengths determined by the measured shift of the fluorescence emissions spectrum due to background fluorescence emissions, and in a plane oriented 54.7° from the vertical, the fluorescence emission intensity in the plane at $\lambda_2$ ($I_{M2}$), whereby the value of $I_{M2}$ is proportional to the total fluorescence emission intensity at $\lambda_2$ ($I_{tot2}$), regardless of the degree of polarization of the fluorescence emitted by the sample;

(d) determining $I_{tot2}$ from $I_{M2}$;

(e) determining from $I_{P1}$, $I_{T1}$, and $I_{tot2}$ the polarized fluorescence emission intensities in the first plane ($I_{P1B}$) and the second plane ($I_{T1B}$) emitted by the extracellular background material at $\lambda_1$;

(f) subtracting $I_{P1B}$ from $I_{P1}$ to obtain a first value ($I_{P1F}$) and subtracting $I_{T1B}$ from $I_{T1}$ to obtain a second value ($I_{T1F}$), the emission intensities at $\lambda_1$ in the first and second planes attributable to intracellular fluorescence from the lymphocytes; and (g) determining P from $I_{P1F}$ and $I_{T1F}$.

27. The method of claim 24 wherein the first and second planes are orthogonal.

28. The method of claim 25 wherein the first and second planes are orthogonal.

29. The method of claim 26 wherein the first and second planes are orthogonal.

30. The method of claim 27 wherein the exciting plane-polarized light is vertically polarized and the vertically and horizontally polarized fluorescence emissions from the suspension are measured.

31. The method of claim 28 wherein the exciting plane-polarized light is vertically polarized and the vertically and horizontally polarized fluorescence emissions from the suspension are measured.

32. The method of claim 29 wherein the exciting plane-polarized light is vertically polarized and the vertically and horizontally polarized fluorescence emissions from the suspension are measured.

33. The method of claim 24 wherein $\lambda_2$ is selected so that the absolute value of $((I_{tot1F}/I_{tot1B}) - (I_{tot2F}/I_{tot2B}))$ is maximized, where $I_{tot1F}$ and $I_{tot2F}$ are the total intracellular fluorescence emission intensities from the lymphocytes at $\lambda_1$ and $\lambda_2$ respectively, and where $I_{tot1B}$ and $I_{tot2B}$ are the total fluorescence emission intensities from the extracellular background at $\lambda_1$ and $\lambda_2$ respectively.

34. The method of claim 25 wherein $\lambda_2$ is selected so that the absolute value of $((I_{tot1F}/I_{tot1B}) - (I_{tot2F}/I_{tot2B}))$ is maximized, where $I_{tot1F}$ and $I_{tot2F}$ are the total intracellular fluorescence emission intensities from the lymphocytes at $\lambda_1$ and $\lambda_2$ respectively, and where $I_{tot1B}$ and $I_{tot2B}$ are the total fluorescence emission intensities from the extracellular background at $\lambda_1$ and $\lambda_2$ respectively.

35. The method of claim 26 wherein $\lambda_2$ is selected so that the absolute value of $((I_{tot1F}/I_{tot1B}) - (I_{tot2F}/I_{tot2B}))$ is maximized, where $I_{tot1F}$ and $I_{tot2F}$ are the total intracellular fluorescence emission intensities from the lymphocytes at $\lambda_1$ and $_g2$ respectively, and where $I_{tot1B}$ and $I_{tot2B}$ are the total fluorescence emission intensities from the extracellular background at $\lambda_1$ and $\lambda_2$ respectively.

36. The method of claim 24, 25, or 26 wherein $\lambda_1$ is at the maximum of the fluorescence emission spectrum of the fluorescing lymphocytes.

37. A method for detection of the SCM response of lymphocytes and use of the response in diagnosis of the presence of a condition or disease in a body detectable by an alteration of the SCM response, the method comprising the steps of;

(a) obtaining a sample of lymphocyte-containing body fluid from the body;

(b) separating SCM-responding lymphocytes from the body fluid;

(c) contacting the SCM-responding lymphocytes with an antigen derived from or associated with the disease or condition being tested for thereby to stimulate the lymphocytes;

(d) forming a suspension of the stimulated lymphocytes and a fluorogenic agent precursor;

(e) maintaining the stimulated lymphocytes in the suspension for sufficient time to allow for the penetration of the lymphocytes by the fluorogenic agent precursor and its intracellular enzymatic hydrolysis to a fluorogenic compound, thereby generating stimulated fluor-containing lymphocytes;

(f) exciting the stimulated fluor-containing lymphocytes with plane-polarized light, thereby causing the fluor-containing lymphocytes as well as any extracellular background fluorescent material to fluoresce;

(g) polarizing the resulting fluorescent emissions in two planes, a first plane parallel to the plane of the exciting plane-polarized light and a second plane transverse to the first plane;

(h) measuring the polarized fluorescent emissions in the two planes at a primary wavelength $\lambda_1$ and a secondary wavelength $\lambda_2$, $\lambda_1$ and $\lambda_2$ being chosen such that where $I_{tot1F}$ and $I_{tot2F}$ are the total intracellular fluorescence emission intensities from the lymphocytes at $\lambda_1$ and $\lambda_2$ respectively, and $I_{tot2F}$ are the total intracellular fluorescence emission intensities from the lymphocytes at $\lambda_1$ and $\lambda_2$ respectively, and $I_{tot1B}$ and $I_{tot2B}$ are the total extracellular fluorescence emission intensities at $\lambda_1$ and $\lambda_2$ respectively, $I_{tot1F}/I_{tot1B}$ is unequal to $I_{tot2F}/I_{tot2B}$, whereby the intensities of the polarized fluorescence in the two planes at $\lambda_1$, $I_{P1}$ in the first plane and $I_{T1}$ in the second plane, and at $\lambda_2$, $I_{P2}$ in the first plane and $I_{T2}$ in the second plane, are obtained;

(i) determining F, the fraction of the total intensity of the fluorescence emissions at $\lambda_1$ due to extracellular fluorescence by using $I_{P1}$, $I_{T1}$, $I_{P2}$, and $I_{T2}$, and determining therefrom the polarized emissions in the first plane ($I_{P1B}$) and the second plane ($I_{T1B}$) due to extracellular fluorescence at $\lambda_1$;

(j) subtracting $I_{P1B}$ from $I_{P1}$ to obtain a first value ($I_{P1F}$) and subtracting $I_{T1B}$ from $I_{T1}$ to obtain a second value ($I_{T1F}$) respectively, the polarized emissions in the first and second planes at $\lambda_1$ due only to the intracellular fluorescence from the stimulated, fluor-containing lymphocytes; and (k) obtaining from $I_{P1F}$ and $I_{T1F}$ the SCM response of the fluor-containing lymphocytes to the antigen derived from or associated with the disease or condition being tested for, whereby the SCM response of the lymphocytes is an indication of the presence or absence of the tested for disease or body condition in the body of the donor of the lymphocytes.

38. The method of claim 37 wherein the lymphocyte-containing body fluid is blood.

39. The method of claim 37 wherein the first and second planes are orthogonal.

40. The method of claim 39 wherein the exciting plane-polarized light is vertically polarized and the vertically and horizontally polarized fluorescence emissions from the suspension are measured.

41. The method of claim 37 wherein $\lambda_2$ is selected so that, where $I_{tot1F}$ and $I_{tot2F}$ are the total intracellular fluorescence emission intensities from the lymphocytes at $\lambda_1$ and $\lambda_2$ respectively, and where $I_{tot1B}$ and $I_{tot2B}$ are the total fluorescence emission intensities from the extracellular background at $\lambda_1$ and $\lambda_2$ respectively, the absolute value of $((I_{tot1F}/I_{tot1B}) - (I_{tot2F}/I_{tot2B}))$ is maximized.

42. The method of claim 37 wherein $\lambda_1$ is at the maximum of the fluorescence emission spectrum of the fluorescing lymphocytes.

43. The method of claim 37 wherein $\lambda_1$ is at 510 nm and is selected to be between 515 nm and 520 nm.

44. The method of claim 37 wherein $\lambda_1$ is 510 nm and $\lambda_2$ is selected to be between 515 nm and 525 nm.

45. The method of claim 44 wherein $\lambda_2$ is 515 nm.

46. The method of claim 44 wherein $\lambda_2$ is 525 nm.

47. The method of claim 37 wherein $\lambda_1$ is 527 nm and $\lambda_2$ selected to be between 532 nm and 537 nm.

48. The method of claim 37 where $\lambda_1$ is 527 nm and $\lambda_2$ is selected to be between 532 nm and 542 nm.

49. The method of claim 48 wherein $\lambda_2$ is 532 nm.

50. The method of claim 24, 25, 26, or 37 wherein the fluorogenic agent precursor is fluorescein diacetate.

51. The method of claim 30 or 39 wherein the step of determining $I_{P1B}$ and $I_{T1B}$ comprises obtaining from $I_{P1}$, $I_{T1}$, $I_{P2}$, and $I_{T2}$ the total fluorescence emissions of the sample at $\lambda_1$ and $\lambda_2$, $I_{tot1}$ and $I_{tot2}$, in accordance with the following relationship:

$$I_{tot\lambda} = I_{P1} + 2(I_{T1} \times G),$$

wherein $I_{tot\lambda}$ is the total intensity of the fluorescence emissions from the suspension at the wavelength $\lambda$, with $\lambda$ being equal to $\lambda_1$ or $\lambda_2$, I, and $I_{P1}$ are either $I_{P1}$ and $I_{T1}$ or $I_{P2}$ and $I_{T2}$ depending upon the value of $\lambda$ chosen, and G is a correction factor for the unequal transmission of the vertically and horizontally polarized fluorescence emissions through the optical system of a fluorescence measuring instrument.

52. The method of claim 51 wherein the step of determining $I_{P1B}$ and $I_{T1B}$ further comprises determining a factor F representing the fraction of the total intensity of the fluorescence emissions at $\lambda_1$, due to background fluorescence by the relationship:

$$F = \frac{K_b - Q}{K_b - K_a}$$

wherein:
(i) $K_a$ is a ratio obtained by dividing the total extracellular fluorescence emission intensity for the background at $\lambda_2$, $I_{tot2B}$, by the total extracellular fluorescence emission intensities for the background at $\lambda_1$, $I_{tot1B}$;
(ii) $K_b$ is a ratio obtained by dividing the total intracellular fluorescence emission intensity for the lymphocytes at $\lambda_2$, $I_{tot2F}$, by the total intracellular fluorescence emission intensity for the lymphocytes at $\lambda_1$, $I_{tot1F}$, the determination of $K_a$ and $K_b$ requiring separation of the lymphocytes and the extracellular background, the determination of $K_a$ and $K_b$ being made for at least one sample separate from the sample of lymphocytes on which the measurement of polarized fluorescence emissions is made, $K_a$ and $K_b$ being constants for the particular instrumentation and fluorogenic agent precursor used; and
(iii) Q is the ratio of $I_{tot2}$ divided by $I_{tot1}$, Q varying with the relative contributions to fluorescence of the lymphocytes and the extracellular background.

53. The method of claim 52 wherein the values of $I_{P1B}$ and $I_{T1B}$ are determined from the factor F according to the relationships:

$$I_{P1B} = \frac{I_{tot1} \times F}{1 + 2(1 - P_k/1 + P_k)},$$

and $$I_{T1B} = \frac{I_{tot1} \times F}{(2 + (1 + P_k/1 - P_k)) \times G},$$

where $P_k$ is a constant defined by the relationship:

$$P_k = \frac{I_{P1BS} - G \times I_{T1BS}}{I_{P1BS} + G \times I_{T1BS}},$$

wherein $I_{P1BS}$ and $I_{T1BS}$ are the vertically and horizontally polarized fluorescence emission intensities, respectively, at $\lambda_1$, of a separate solution of the fluorogenic agent precursor from which the lymphocytes have been filtered, and G is a correction factor for the unequal transmission of the vertically and the horizontally polarized fluorescence emissions through the optical system of a fluorescence measuring instrument.

54. The method of claim 53 further comprising the steps of:
(a) determining the following at a second secondary wavelength, $\lambda_3$, within the range of wavelengths determine by the shift of the fluorescence emission spectrum due to extracellular fluorescence emissions:
  (i) the vertically and horizontally polarized fluorescence emissions from the suspension, $I_{P3}$ and $I_{T3}$;
  (ii) the total extracellular fluorescence emission intensity from the background, $I_{tot3B}$, the lymphocytes having been removed from the suspension; and
  (iii) the total intracellular fluorescence emission intensity from the lymphocytes, $I_{tot3F}$;
(b) determining from $I_{P3}$, $I_{T3}$, $I_{tot3B}$, $I_{tot3F}$, $I_{P1}$, $I_{T1}$, $I_{tot1B}$, and $I_{tot1F}$, a second value of the factor F, $F_2$;
(c) determining the average value of the factor F, $F_{av}$, from the first value of F determined at $\lambda_1$ and $\lambda_2$, $F_1$, and from $F_2$; and
(d) using $F_{av}$ in determining $I_{P1B}$ and $I_{T1B}$.

* * * * *